United States Patent [19]

Adachi et al.

[11] Patent Number: 6,100,421
[45] Date of Patent: Aug. 8, 2000

[54] HETEROCYCLE-SUBSTITUTED BENZENE DERIVATIVES AND HERBICIDES

[75] Inventors: Hiroyuki Adachi, Odawara; Masao Yamaguchi, Hiratsuka; Takahiro Sagae, Niigata; Masami Koguchi, Odawara; Kazuyuki Tomita, Shizuoka; Takashi Kawana, Minamiashigara; Akihiro Takahashi, Minamiashigarashi, all of Japan

[73] Assignee: Nippon Soda Co., Ltd., Tokyo, Japan

[21] Appl. No.: 09/359,444

[22] Filed: Jul. 22, 1999

Related U.S. Application Data

[63] Continuation-in-part of application No. 09/155,086, Sep. 18, 1998.
[51] Int. Cl.⁷ .................................................. C07C 321/00
[52] U.S. Cl. .................................................. 560/9
[58] Field of Search .................................................. 560/9

[56] References Cited

U.S. PATENT DOCUMENTS 5,939,360  8/1999  Adachi et al. .......................... 504/271

FOREIGN PATENT DOCUMENTS 6-271562  4/1995  Japan .
96/26200  8/1996  WIPO .

*Primary Examiner*—Deborah C. Lambkin
*Attorney, Agent, or Firm*—Joseph C. Mason, Jr.; Dennis G. LaPointe; Mason & Associates, PA

[57] ABSTRACT

The present invention is directed to a benzoic acid derivative methyl 3-formyl-4-methanesulfonyl-2-methylbenzoate. The compound is useful as a starting material for herbicide manufacture.

1 Claim, No Drawings

HETEROCYCLE-SUBSTITUTED BENZENE DERIVATIVES AND HERBICIDES

This application is a CIP of U.S. Ser. No. 09/155,086 Sep. 18, 1998.

FIELD OF INVENTION

The present invention relates to novel heterocycle-substituted benzene derivatives and herbicides.

Prior Art

It is disclosed in Japanese Patent Laid-open Nos. Hei 3-255047 and Hei 6-271562, WO 94/04524, etc. that 2-benzoylcyclohexane-1,3-dione compounds which are similar to the compounds being specified in the present invention have herbicidal activity. Whereas, compounds represented by the following chemical formula [III] are disclosed in WO 96/26200.

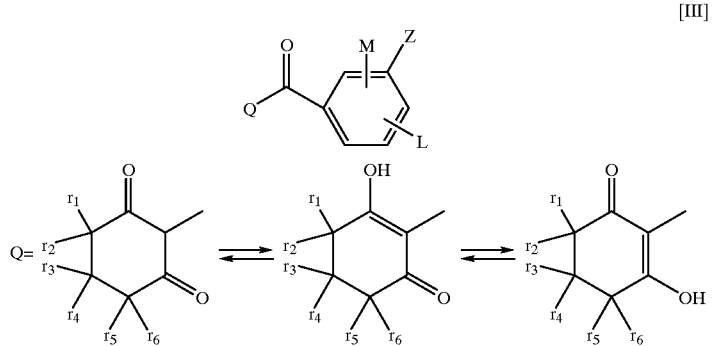

[III]

wherein $r_1$ through $r_6$ represent each independently hydrogen, $C_1$–$C_6$ alkyl, $C_1$–$C_6$ alkylthio, $C_3$–$C_6$ cycloalkyl or the like; M and L represent each independently hydrogen, $C_1$–$C_6$ alkyl, $C_1$–$C_6$ alkenyl, halogeno or the like; and Z represents 5 to 6-membered saturated or unsaturated heterocyclic group.

DISCLOSURE OF INVENTION

It is an object of the present invention to provide compounds which can be advantageously manufactured in an industrial scale, giving more firm herbicidal efficacy with less doses, being highly safe and are useful as a herbicide having excellent crop selectivity.

The present invention is directed to a herbicide containing one or more of heterocycle-substituted benzene derivatives and/or salts thereof, represented by a general formula [I];

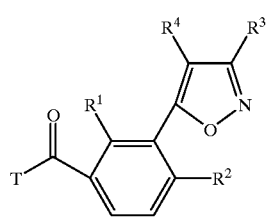

[I]

wherein $R^1$ represents halogeno, $C_1$–$C_6$ alkyl, $C_1$–$C_6$ alkoxy, nitro, cyano, $C_1$–$C_6$ haloalkyl, $C_1$–$C_6$ alkylthio, $C_1$–$C_6$ alkylsulfinyl or $C_1$–$C_6$ alkylsulfonyl;

$R^2$ represents halogeno, nitro, cyano, $C_1$–$C_6$ alykl, $C_1$–$C_6$ alkoxy, $C_1$–$C_6$ haloalkyl, $C_1$–$C_6$ haloalkoxy, $C_1$–$C_6$ alkylthio, $C_1$–$C_6$ alkylsulfinyl or $C_1$–$C_6$ alkylsulfonyl;

$R^3$ and $R^4$ represent each independently hydrogen, $C_1$–$C_6$ alkyl or $C_1$–$C_6$ haloalkyl;

T represents cyclohexanedione-1,3-dione cyclic group represented by a general formula [II];

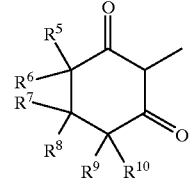

[II]

wherein $R^5$, $R^6$, $R^7$, $R^8$, $R^9$ and $R^{10}$ represent each independently hydrogen, halogeno, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ alkylsulfinyl, $C_1$–$C_6$ alkylsulfonyl, optionally-substituted phenyl, $C_1$–$C_6$ alkylthio $C_1$–$C_6$ alkyl, $C_1$–$C_6$ alkylsulfinyl $C_1$–$C_6$ alkyl, $C_1$–$C_6$ alkylsulfonyl $C_1$–$C_6$ alkyl, optionally-substituted phenylthio $C_1$–$C_6$ alkyl, optionally-substituted phenylsulfinyl $C_1$–$C_6$ alkyl, optionally-substituted phenylsulfonyl $C_1$–$C_6$ alkyl, $C_1$–$C_6$ alkoxy $C_1$–$C_6$ alkyl, optionally-substituted phenyl $C_1$–$C_6$ alkyloxy $C_1$–$C_6$ alkyl, $C_1$–$C_6$ alkylcarbonyloxy $C_1$–$C_6$ alkyl, hydroxy $C_1$–$C_6$ alkyl, di-($C_1$–$C_6$ alkoxy) $C_1$–$C_6$ alkyl, $C_1$–$C_6$ alkoxycarbonyl, cyano, formyl, hydroxyimino $C_1$–$C_6$ alkyl, $C_1$–$C_6$ alkoxyimino $C_1$–$C_6$ alkyl, $C_2$–$C_4$ alkenyloxyimino $C_1$–$C_6$ alkyl, $C_2$–$C_4$ alkynyloxyimino $C_1$–$C_6$ alkyl, $C_1$–$C_6$ haloalkoxyimino $C_1$–$C_6$ alkyl, $C_2$–$C_6$ haloalkenyloxyimino $C_1$–$C_6$ alkyl or $C_2$–$C_4$ haloalkynyloxyimino $C_1$–$C_6$ alkyl; or, ($R^5$ or $R^6$) and ($R^7$ or $R^8$), ($R^7$ or $R^8$) and ($R^9$ or $R^{10}$) may form in together either methylene or $C_2$–$C_5$ alkylene chain.

Now, the present invention is further described in detail hereinbelow.

The present invention is directed to a herbicide containing one or more of heterocycle-substituted benzene derivatives and salts thereof, represented by a general formula [I] as the active principle.

In the formula [I], $R^1$ represents halogeno, such as fluorine, chlorine and bromine, $C_1$–$C_6$ alkyl, such as methyl, ethyl, propyl, isopropyl, butyl and t-butyl, $C_1$–$C_6$ alkoxy, such as methoxy, ethoxy, propoxy and isopropoxy, $C_1$–$C_6$ haloalkyl, nitro, cyano, chloromethyl, fluoromethyl, dichloromethyl, difluoromethyl and trifluoromethyl, $C_1$–$C_6$ alkylthio, such as methylthio, ethylthio, propylthio and isopropylthio, $C_1$–$C_6$ alkylsulfinyl, such as methylsulfinyl, ethylsulfinyl, propylsulfinyl and isopropylsulfinyl, or $C_1$–$C_6$ alkylsulfonyl, such as methylsulfonyl, ethylsulfonyl, propylsulfonyl and isopropylsulfonyl;

$R^2$ represents halogeno, such as fluorine, chlorine and bromine, nitro, cyano, $C_1$–$C_6$ alkyl, such as methyl, ethyl, propyl and isopropyl, $C_1$–$C_6$ alkoxy, such as methoxy, ethoxy, propoxy and isopropoxy, $C_1$–$C_6$ haloalkyl, such as chloromethyl, fluoromethyl, bromomethyl, dichloromethyl, difluoromethyl, trichloromethyl and trifluoromethyl, $C_1$–$C_6$ haloalkoxy such as trifluoromethoxy, $C_1$–$C_6$ alkylthio, such as methylthio, ethylthio, propylthio and isopropylthio, $C_1$–$C_6$ alkylsulfinyl, such as methylsulfinyl, ethylsulfinyl, propylsulfinyl and isopropylsulfinyl, or $C_1$–$C_6$ alkylsulfonyl, such as methylsulfonyl, ethylsulfonyl, propylsulfonyl and isopropylsulfonyl;

$R^3$ and $R^4$ each independently represent $C_1$–$C_6$ alkyl, such as methyl, ethyl, propyl and isopropyl, $C_1$–$C_6$ haloalkyl, such as chloromethyl, fluoromethyl, bromomethyl, dichloromethyl, difluoromethyl, trichloromethyl and trifluoromethyl;

T represents cyclohexanedione cyclic group represented by a general formula [II];

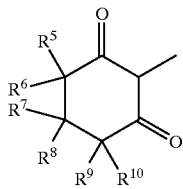

[II]

wherein $R^5$, $R^6$, $R^7$, $R^8$, $R^9$ and $R^{10}$ represent each independently hydrogen, halogeno, such as fluorine, chlorine and bromine, $C_1$–$C_6$ alkyl, such as methyl, ethyl, propyl and isopropyl, $C_1$–$C_6$ haloalkyl, such as chloromethyl, bromomethyl, dichloromethyl, chloroethyl, difluoromethyl, trifluoromethyl and trichloromethyl, $C_1$–$C_6$ alkoxy, such as methoxy, ethoxy, propoxy, isopropoxy, butoxy and t-butoxy, $C_1$–$C_6$ haloalkoxy, such as trifluoromethoxy and trichloromethoxy, $C_1$–$C_6$ alkylthio, such as methylthio, ethylthio, propylthio and isopropylthio, $C_1$–$C_6$ alkylsulfinyl, such as methylsulfinyl, ethylsulfinyl, propylsulfinyl and isopropylsulfinyl, $C_1$–$C_6$ alkylsulfonyl, such as methylsulfonyl, ethylsulfonyl, propylsulfonyl and isoporpylsulfonyl, phenyl of which optional position in the benzene ring being optionally-substituted with any of halogeno, such as fluorine, chloride and bromine, $C_1$–$C_6$ alkyl such as methyl, $C_1$–$C_6$ alkoxy, such as methoxy and ethoxy, nitro and cyano; $C_1$–$C_6$ alkylthio $C_1$–$C_6$ alkyl, such as methylthiomethyl, methylthioethyl, methylthiopropyl, ethylthiomethyl, ethyl thioethyl, 2-ethylthiopropyl and 3-ethylthiopropyl; $C_1$–$C_6$ alkylsulfinyl $C_1$–$C_6$ alkyl, such as methylsulfinylmethyl, methylsulfinylethyl, methylsulfinylpropyl, ethylsulfinylmethyl, ethylsulfinylethyl, 2-ethylsulfinylpropyl and 3-ethylsulfinylpropyl; $C_1$–$C_6$ alkylsulfonyl $C_1$–$C_6$ alkyl, such as methylsulfonylmethyl, methylsulfonylethyl, methylsulfonyipropyl, ethylsulfonylmethyl, ethylsulfonylethyl, 2-ethylsulfonylpropyl and 3-ethylsulfonylpropyl; phenylthio $C_1$–$C_6$ alkyl of which an optional position of the benzene ring being optionally substituted with any of halogeno, such as fluorine, chlorine and bromine, $C_1$–$C_6$ alkyl such as methyl, $C_1$–$C_6$ alkoxy, such as methoxy and ethoxy, nitro and cyano, such as phenylthiomethyl, phenylthioethyl and phenylthiopropyl; phenylsulfinyl $C_1$–$C_6$ alkyl of which an optional position of the benzene ring being optionally substituted with any of halogeno, such as fluorine, chlorine and bromine, $C_1$–$C_6$ alkyl such as methyl, $C_1$–$C_6$ alkoxy, such as methoxy and ethoxy, nitro and cyano, such as phenylsulfinylmethyl, phenylsulfinylethyl and phenylsulfinylpropyl; phenylsulfonyl $C_1$–$C_6$ alkyl of which an optional position of the benzene ring being optionally substituted with any of halogeno, such as fluorine, chlorine and bromine, $C_1$–$C_6$ alkyl such as methyl, $C_1$–$C_6$ alkoxy, such as methoxy and ethoxy, nitro and cyano, such as phenylsulfonylmethyl, phenylsulfonylethyl and phenylsulfonylpropyl; $C_1$–$C_6$ alkoxy $C_1$–$C_6$ alkyl, such as methoxymethyl, methoxyethyl, methoxypropyl, ethoxymethyl, ethoxyethyl, propoxymethyl and propoxyethyl; phenyl $C_1$–$C_6$ alkyloxy $C_1$–$C_6$ alkyl of which an optional position of the benzene ring being optionally substituted with any of halogeno, such as fluorine, chlorine and bromine, $C_1$–$C_6$ alkyl such as methyl, $C_1$–$C_6$ alkoxy, such as phenylmethoxymethyl, phenylethoxymethyl, phenylpropoxymethyl, phenylmethoxyethyl and phenylethoxyethyl; $C_1$–$C_6$ alkylcarbonyloxy $C_1$–$C_6$ alkyl, such as methoxycarbonyloxymethyl, ethoxycarbonyloxymethyl and methoxycarbonyloxy ethyl; hydroxy $C_1$–$C_6$ alkyl, such as hydroxymethyl and hydroxyethyl; di-($C_1$–$C_6$ alkoxy) $C_1$–$C_6$ alkyl, such as di-(methoxy) methyl, di-(ethoxy) methyl and di-(methoxy)ethyl; $C_1$–$C_6$ alkoxycarbonyl, such as methoxycarbonyl and ethoxycarbony; cyano; formyl; hydroxyimino $C_1$–$C_6$ alkyl, such as hydroxyiminomethyl, hydroxyiminoethyl and hydroxyiminopropyl; $C_1$–$C_6$ alkoxyimino $C_1$–$C_6$ alkyl, such as methoxyiminomethyl, methoxyiminoethyl, methoxyiminopropyl, ethoxyiminomethyl and ethoxyiminoethyl; $C_2$–$C_4$ alkenyloxyimino $C_1$–$C_6$ alkyl, such as vinyloxyiminomethyl, allyloxyiminomethyl, crotyloxyiminomethyl, allyloxyiminoethyl and allyloxyiminopropyl; $C_2$–$C_4$ alkynyloxyimino $C_1$–$C_6$ alkyl, such as ethynyloxyiminomethyl, ethynyloxyiminoethyl, propalgyloxyiminomethyl and propalgyloxyiminoethy $C_1$–$C_6$ haloalkoxyimino $C_1$–$C_6$ alkyl, such as chloromethoxyiminomethyl, chloromethoxyiminoethyl, chloromethoxyiminopropyl, dichloroethoxyiminomethyl, chloroethoxyiminoethyl, fluoromethoxyiminomethyl, fluoromethoxyimi noethyl, trifluoroethoxyiminomethyl and trifluoroethoxyiminoethyl; $C_2$–$C_4$ haloalkenyloxyimno $C_1$–$C_6$ alkyl, such as chloroallyloxyiminomethyl, chloroallyloxyiminoethyl, fluoroallyloxyiminomethyl, fluoroallyloxyimino ethyl, bromoallyloxyiminomethyl, chlorobutenyloxyiminomethyl and chlorobutenyloxyiminoethyl; or $C_2$–$C_4$ haloalkynyloxyimino $C_1$–$C_6$ alkyl, such as chloroethynyloxyiminomethyl, chloroethynyloxyiminoethyl, chloropropagyloxyiminomethyl and chloropropagyloxyiminomethyl; and, ($R^5$ or $R^6$) and ($R^7$ or $R^8$), and ($R^7$ or $R^8$) and ($R^9$ or $R^{10}$) may in together form an $C_1$–$C_5$ alkylene chain, such as methylene, ethylene and propylene, respectively.

As more preferable examples for the group represented by T, any of cyclohexanedione cyclic groups as described below can be given.

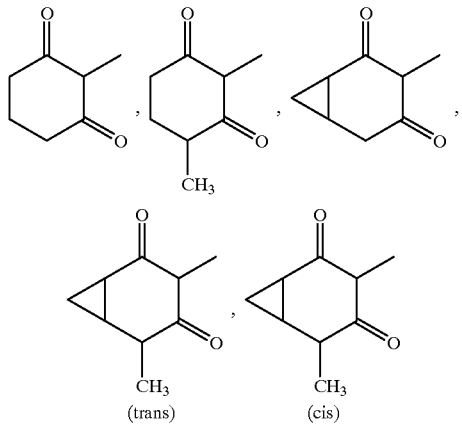

In the group represented by T, the tautomers as shown below can be also included, and it should be noted that all of these tautomers fall within the compounds specified in the present invention.

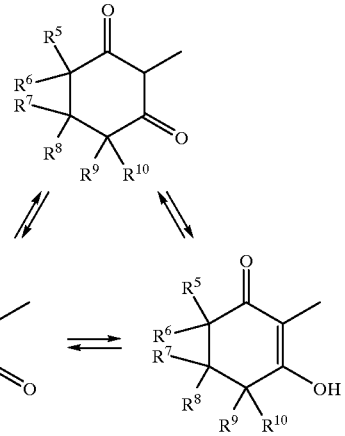

Manufacturing of Compounds

The compounds of the present invention can be manufactured according to the following manufacturing processes.

Manufacturing Process (i);

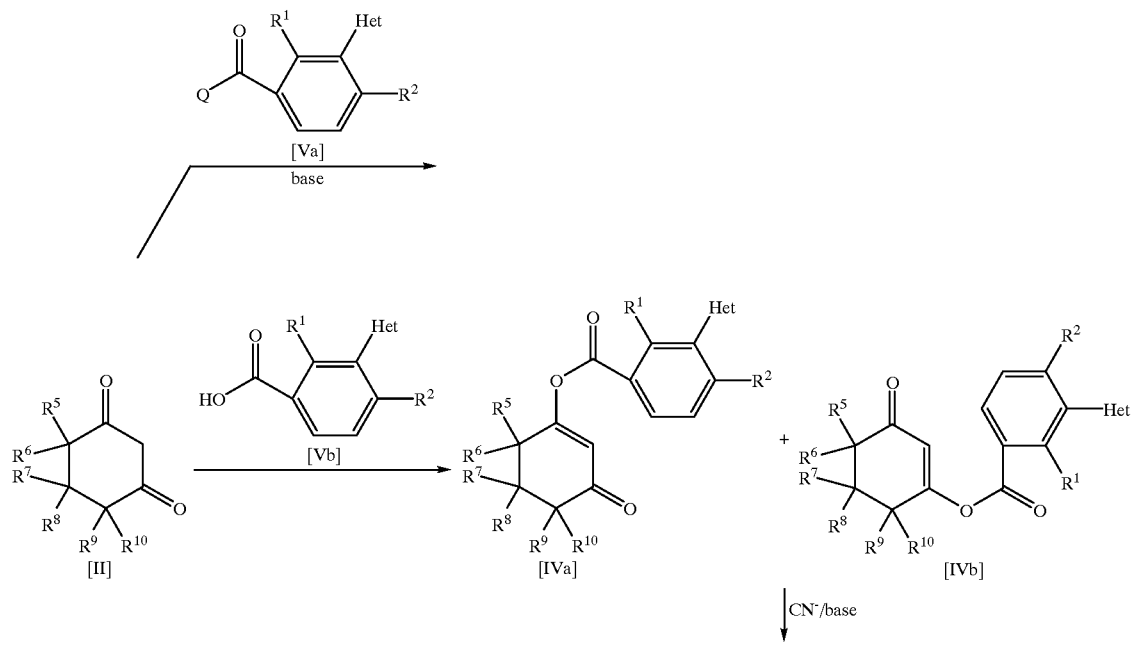

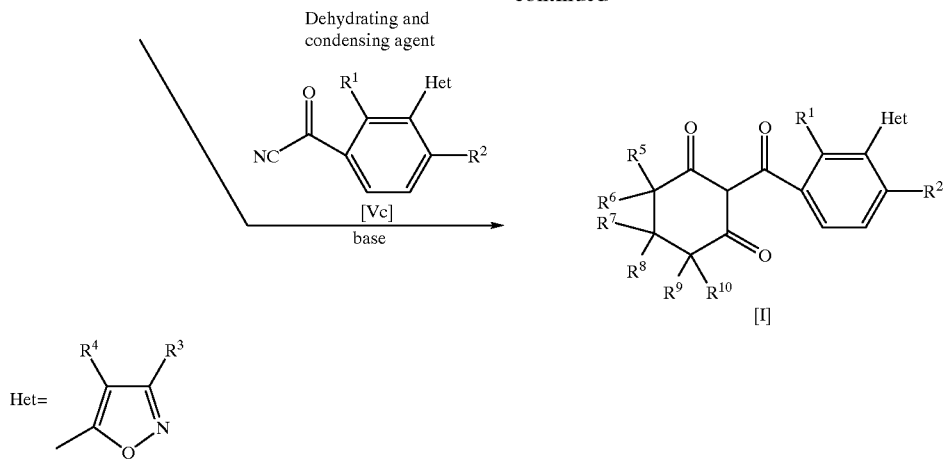

wherein $R^1$, $R^2$, $R^3$, $R^4$, $R^5$, $R^6$, $R^7$, $R^8$, $R^9$ and $R^{10}$ are as defined above, and Q represents halogeno, alkylcarbonyloxy, alkoxycarbonyloxy or benzoyloxy.

In the manufacturing process described above, a compound of formula [IVa] and a compound of formula [IVb] can be obtained by allowing both of compounds of formula [II] and formula [Va] each in an amount of 1 mole or either one of them in an excess amount to a reaction in the presence of a base in an amount of 1 mole or in an excess amount. As the base to be used in the reaction, an alkali metal hydrate, such as KOH and NaOH, an alkali metal carbonate, an alkaline earth metal hydroxide, an alkaline earth metal carbonate, tri($C_1$–$C_6$ alkyl)amine, pyridine, sodium phosphate and the like can be used, and as the solvent to be used in the reaction, $H_2O$, methylene chloride, chloroform, toluene, ethyl acetate, N,N-dimethylformamide (DMF), tetrahydrofuran (THF), dimethoxy ethane, acetonitrile and the like can be used. The reaction mixture is kept to be stirred until the completion of the reaction at a temperature ranging from 0 to 50° C. Further, the compounds of formulas [IVa] and [IVb] can be also obtained through a reaction in two phase solvent system and using a phase transfer catalyst such as quaternary ammonium salts. The compounds of formulas [IVa] and [IVb] are also obtainable by allowing a compound of formula [II] and a compound of formula [Vb] to a reaction with dicyclohexycarbodiimide (DCC). As examples for the solvent to be used in the reaction with DCC, methylene chloride, chloroform, toluene, ethyl acetate, DMF, THF, dimethoxy ethane, acetonitrile and the like are given. The reaction mixture is kept stirring at a temperature of from −10 to 50° C. until the completion of the reaction. The reacted-product is treated according to a method customarily-employed.

A rearrangement reaction is carried out in the presence of a cyano compound and a mild base. For example, a compound of formula [IVa] and a compound of formula [IVb] each in an amount of 1 mole are allowed to a reaction with a base in an amount of 1 to 4 mole, more preferably 1 to 2 mole, and a cyano compound in an amount of 0.01 to 0.5 mole, more preferably 0.05 to 0.2 mole. For the base to be used in this reaction, any of the bases as described above can be used. Whereas, for the cyano compound to be used in the reaction, any of potassium cyanide, sodium cyanide, acetone cyanohydrin, hydrogen cyanide, polymer carrying potassium cyanide and the like can be used. Further, the reaction can be completed in a shorter time by means of adding a small amount of a phase transfer catalyst such as crown ether. The reaction is performed at a temperature lower than 80° C., more preferably at temperature of from 20 to 40° C. As the examples for the solvent to be used, 1,2-dichloro ethane, toluene, acetonitrile, methylene chloride, ethyl acetate, DMF, methyl isobutyl ketone, THF, dimethoxy ethane and the like can be given.

Alternatively, the similar rearrangement reaction can be proceeded by means of adding the cyano compound and the base as described above into the reaction system without taking the isolation process for the compounds of formulas [IVa] and [IVb].

Further, the compound of formula [I] can be also obtained by allowing a compound of formula [II] to a reaction with a compound of formula [Vc] according to the method as described below in the presence of a base and with a Lewis acid if required. As examples for the base to be used in the reaction, alkali metal hydroxides, such as KOH and NaOH, alkali earth metal hydroxides, tri($C_1$–$C_6$ alkyl)amine, pyridine, sodium carbonate, sodium phosphate and the like can be given. For the appropriate Lewis acid, zinc chloride, aluminium trichloride and the like can be used, however, it is more preferable to use zinc chloride. The reaction is proceeded at an appropriate temperature in a range of from −20 to the boiling point of a solvent used in an organic solvent, such as acetonitrile and methylene chloride.

Manufacturing Process (ii)

Alternatively, the objective compounds of formulas [Ib] and [Ic], wherein a substituent on a cyclohexane ring is replaced, can be prepared by means of using the compound of formula [Ia] prepared as described above according to the following process;

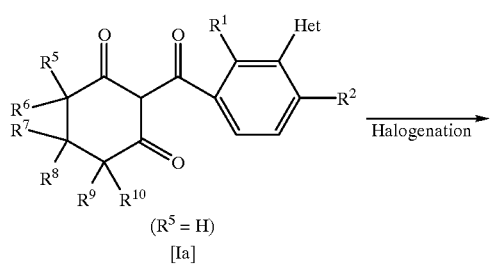

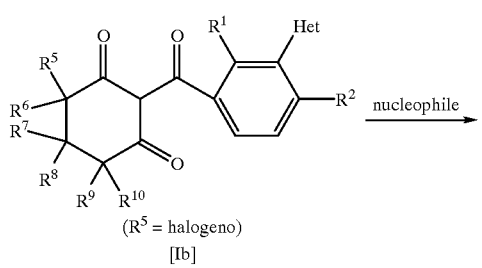

($R^5$ = halogeno)

[Ib]

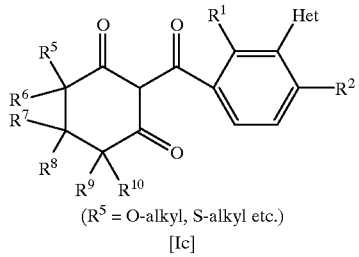

($R^5$ = O-alkyl, S-alkyl etc.)

[Ic]

wherein $R^1$, $R^2$, $R^5$, $R^6$, $R^7$, $R^8$, $R^9$, $R^{10}$ and Het are as defined above.

In the process described above, a halogenized trione-form of formula [Ib] can be prepared by allowing a compound of formula [Ia] to a reaction with an halogenating agent, such as phenyltrimethylammonium tribromide and dibromo meldoram's acid, in an inactive solvent at an appropriate temperature in a range of from 0° C. to the boiling point of the solvent, more preferably from an ambient temperature to 50° C., for several hours to several dozen hours. As examples for the solvent used in the reaction, methylene chloride, benzene, ethyl acetate, THF, acetonitrile, dimethoxy ethane and the like can be given. Furthermore, the objective compounds of formula [Ic] are also obtainable by allowing the halogenated trione of formula [Ib] to a reaction with a nucleophilic reagent in the presence of a base.

Manufacturing Process (iii)

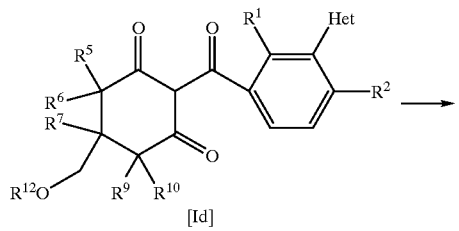

[Id]

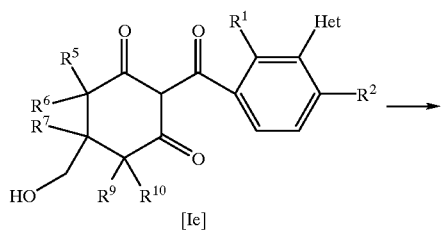

[Ie]

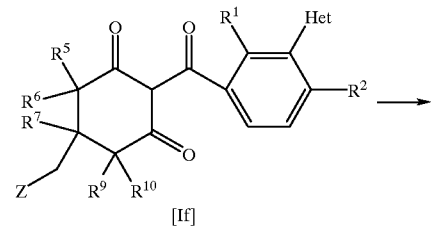

[If]

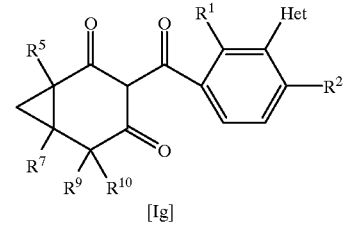

[Ig]

In the reaction formula described above, $R^1$, $R^2$, $R^5$, $R^6$, $R^7$, $R^9$, $R^{10}$ and Het are as defined above, $R^{12}$ represents lower branched or unbranched-alkyl, aralkyl or acetyl, and Z represents an eliminating group, such as halogeno, alkylsulfonate and arylsulfonate.

Therefore, a compound of formula [Ie] can be prepared by subjecting a compound of formula [Id] to a reaction with any of hydrohalogenoacid, such as hydrochloric acid and hydrobromic acid, trifluoroacetic acid and boron tribromide, or to hydrogenolysis or hydrolysis with an alkali, and subsequently to hydrolysis if required.

Furthermore, the compound of formula [Ie] can be transformed to a compound of formula [If] by subjecting it to any process of halogenation, alkylsulfonate formation and arylsulfonate formation according to a customarily-employed method. By allowing the compound of formula [If] to a reaction in a solvent in the presence of a base in an amount more than 1 mole at a temperature in a range of from −20° C. to a boiling point of a solvent used, more preferably from an ambient temperature to 100° C., for a period of from 30 minutes to several dozen hours, a compound of formula [Ig] can be prepared.

As examples for the base to be used as described above, alkali metal hydroxides, such as KOH and NaOH, alkaline earth metal hydroxides, tri-($C_1$–$C_6$ alkyl)amine, pyridine, 1,8-diaza-bicyclo[5,4,0]unde-7-cene (DBU), t-BuOK, triton B, sodium carbonate, sodium phosphate and the like can be given, and as the solvent, $H_2O$, alcohol, methylene chloride, benzene, toluene, ethyl acetate, DMF, THF, dimethoxy ethane, acetonitrile and the like can be used either alone or the mixture.

Manufacturing Process (iv)

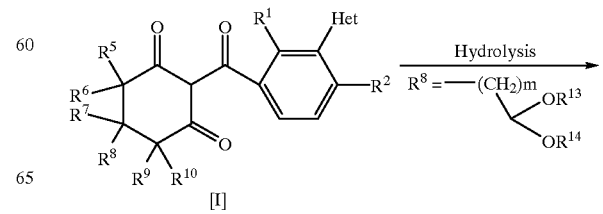

[I]

-continued

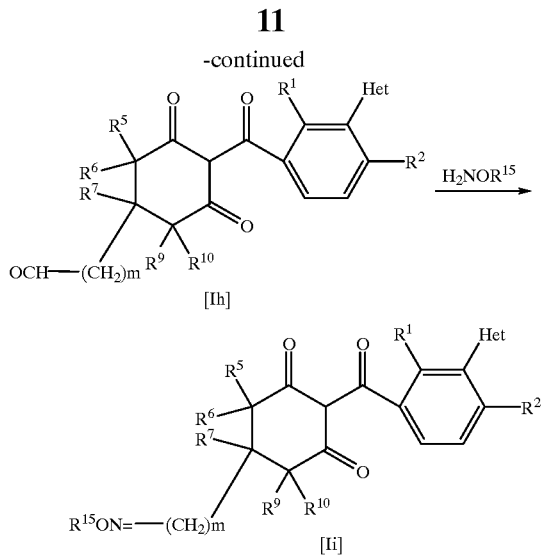

In the reaction formula described above, $R^1$, $R^2$, $R^5$, $R^6$, $R^7$, $R^8$, $R^9$, $R^{10}$ and Het are as defined above. $R^{13}$ and $R^{14}$ represents a lower alkyl, $R^{15}$ represents hydrogen, $C_1-C_6$ alkyl, $C_2-C_4$ alkenyl, $C_2-C_4$ alkynyl, $C_1-C_6$ haloalkyl, $C_2-C_4$ haloalkenyl or $C_2-C_4$ haloalkynyl, and m represents 0 or 1.

Compounds of formula [Ih] can be manufactured from a compound of formula [I] according to a method customarily-employed. Then, compounds of formula [Ii] can be manufactured by allowing the compound of formula [Ih] to a reaction in an solvent in the presence of a compound represented by a formula; $H_2NOR^{15}$ in an amount more than equivalent mole at a temperature in a range of from −20° C. to a boiling point of a solvent used, more preferably from an ambient temperature to 100° C., for a period of from 30 minutes to several dozen hours. The reaction can be completed in a shorter time when a small amount of acid catalyst such as sulfuric acid. As examples for the solvent described above, $H_2O$, alcohol, methylene chloride, benzene, toluene, ethyl acetate, DMF, THF, dimethoxy ethane, acetonitrile and the like can be given.

Cyclic diones represented by a general formula [II] can be manufactured according to a manufacturing process publicly-known. Again, substituted-benzoic acids of formula [Va] as described above can be also manufactured according to a manufacturing process publicly-known.

The compounds of the present invention of formula [I] include various types of tautomers as shown below. All of these tautomers fall within the compounds according to the present invention.

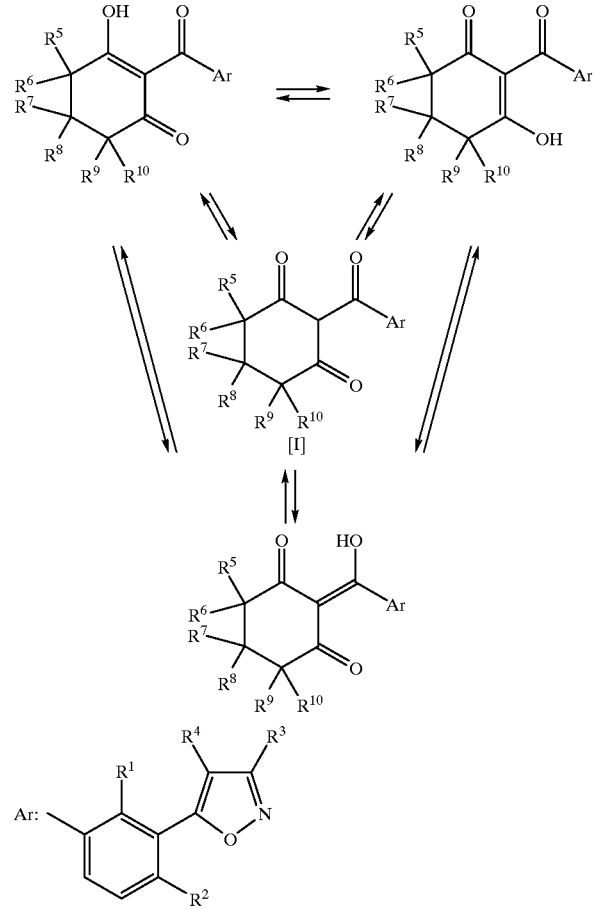

The compounds in aldehyde-form of formula (3) and the compounds in carboxylate-form of formula (4), which are important synthetic intermediates for manufacturing the compounds of the present invention, can be manufactured according to the following manufacturing process;

Further, the intermediates described hereunder can be prepared by using the aldehyde-form compound of formula (3) and the carboxylate-form compounds of formula (4) as described above.

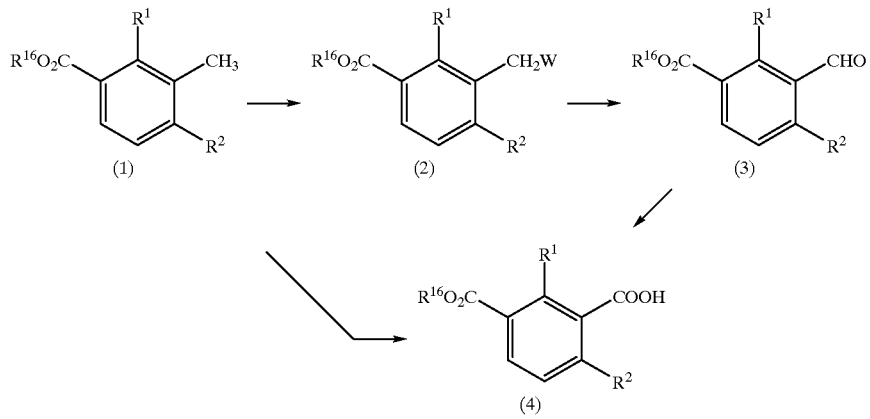

wherein $R^1$ and $R^2$ are as defined above, $R^{16}$ represents hydrogen or a lower alkyl, and W is halogeno.

The aldehyde-form compounds of formula (3) can be prepared according to a method customarily-known, for example, by allowing the toluene derivative of formula (1)

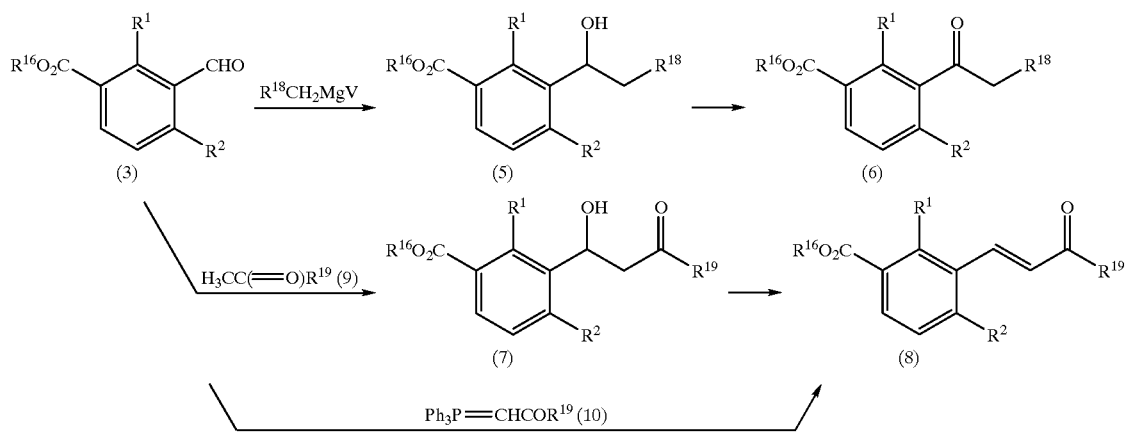

to a reaction with either halogeno, such as chlorine and bromine, or a halogenating agent, such as N-bromosuccinimide and N-chlorosuccinimide, in the presence of either light or radical reaction initiator such as benzoyl peroxide to obtain a benzyl halide derivative of formula (2) and subsequently by employing the method described in J. Am. Chem. Soc., 71, 1767 (1949), which is to allow the benzyl halide derivative to a reaction with an alkali metal salt of nitroalkane such as 2-nitropropane in an alcohol, such as methanol and ethanol, at a temperature of from 0° C. to a boiling point of the solvent used.

Whereas, carboxylate-form compounds of formula (4) can be prepared either via oxidation process of a toluene derivative of formula (1) with potassium permanganate or the like or a customarily-known method, such as the oxidation of the aldehyde-form of formula (3) by using any of Jones reagent, chromic acid, potassium permanganate and the like.

In the reaction process described above, $R^1$, $R^2$ and $R^{16}$ are as defined above, $R^{17}$ and $R^{18}$ each independently represents hydrogen or a lower alkyl, V represents halogeno, and $R^{19}$ represents a lower alkyl.

The acyl-form of formula (6) corresponding to the aldehyde-form of formula (3) is obtainable by firstly allowing the aldehyde-form to a reaction with a Grignard reagent to produce the alcohol-form of formula (5) and subsequently allowing the alcohol-form (5) to the oxidation process using any of activated manganese dioxide, chromic acid and the like.

Also, the vinyl ketone-form of formula (8) can be manufactured according to a customarily-known process, for example, a process described in Org. Syn., Coll. Vol. 1, 77 (1941), by firstly allowing the aldehyde-form of formula (3) to a reaction with the methyl ketone-form of formula (9) in water for 1 to 50 hours in the presence of a catalyst at a temperature of from 0 to 50° C. to produce the aldol-form of formula (7) and by subsequently allowing the aldol-form to dehydration process using a catalyst in an appropriate solvent. As examples for the catalyst to be used at the manufacturing of the aldol-form of formula (7), metal hydroxides, such as sodium hydroxide and barium hydroxide, and organic bases, such as piperidine and pyridine, can be given. Whereas, as examples for the catalyst to be used in the dehydration process described above, acids, such as concentrated sulfuric acid and p-toluenesulfonic acid, can be given. And, as examples for the solvent used in the dehydration reaction, hydrocarbons, such as benzene and toluene, and halogenated hydrocarbons, such as dichloromethane and chloroform, can be given.

Alternatively, the vinyl ketone-form of formula (8) can be manufactured by allowing the aldehyde-form of formula (3) to a reaction with the phosphorane-form of formula (10) in an appropriate solvent at a temperature of from an ambient temperature to a boiling point of the solvent used for a period of from 10 minutes to 30 hours.

The β-diketone-form of formula (11) can be manufactured according to a process as described hereunder.

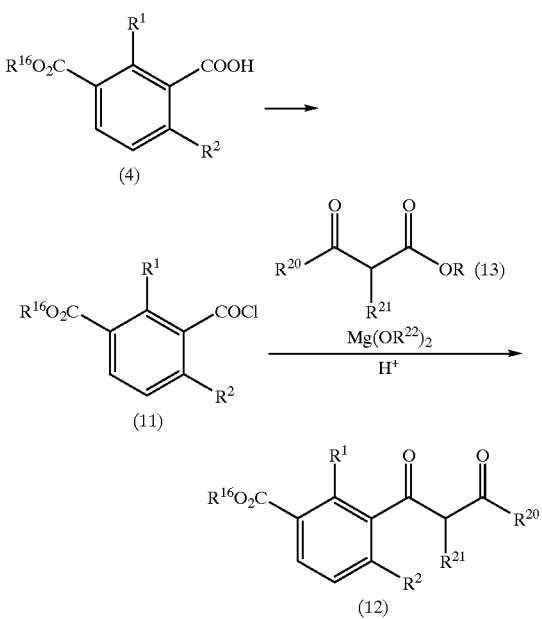

In the process described above, $R^1$, $R^2$ and $R^{16}$ are as defined above, and R, $R^{20}$, $R^{21}$ and $R^{22}$ each independently represent a lower alkyl.

Where, at first, an intermediate, carbonyl chloride of formula (11) is manufactured by allowing the carboxylate-form of formula (4) to a reaction with a chlorinating agent, such as phosgene, thionyl chloride and oxalyl chloride, in an inactive solvent, such as hydrocarbons including benzene, toluene, etc. and halogenated hydrocarbons including methylene chloride, chloroform, etc. Then, β-keto ester-form of formula (13) is reacted with magnesium alcoholate to prepare the magnesium salt thereof. The β-diketone-form of formula (11) is then manufactured by allowing the magnesium salt to a reaction with the carbonyl chloride of formula (11) according to a customarily-known process.

Now, the process for manufacturing isoxasol intermediates is described hereinbelow.

Manufacturing Process 1

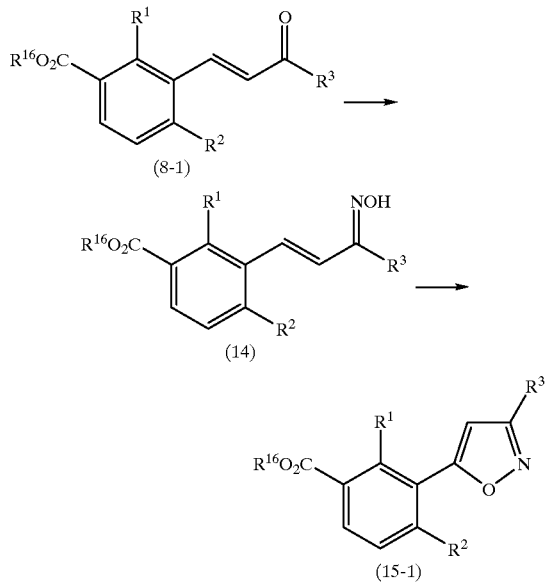

In the process described above, $R^1$, $R^2$ and $R^3$ are as defined above, and $R^{16}$ represents a lower alkyl.

A compound of formula (15-1) can be manufactured by firstly allowing the vinyl ketone-form of formula (8-1) to a reaction with hydroxylamine for a period of from 0.5 to 5 hours in an appropriate solvent at a temperature of form 0° C. to the boiling point of a solvent used to prepare an oxime-form of formula (14) and subsequently subjecting the oxime-form to a ring-closing and oxidation reaction. Said hydroxylamine to be used in said oximation reaction can be allowed to a reaction in a form either sulfate or chloride or after subjecting it to neutrization process by using an appropriate base. As examples for the base used in the neutrization process, carbonates, such as sodium hydrogencarbonate and potassium carbonate, alkali metal hydroxides, such as sodium hydroxide and potassium hydroxide, carboxylates such as sodium acetate, metal alcoholates, such as sodium methylate and sodium ethylate, and organic bases, such as triethylamine and pyridine, can be given. Further, as examples for the solvent usable in this process, alcohols, such as methanol, ethanol and isopropanol, hydrocarbons, such as benzene and toluene, halogenated hydrocarbons, such as dichloromethane and chloroform, ethers, such as THF and dioxane, nutriles like acetonitrile, DMF, pyridine, acetic acid, water and the like can be given, and these examples can be used either alone or as a mixture of 2 or more thereof.

The ring-closing and oxidation reaction of the oxime-form of formula (14) can be proceeded according to the methods disclosed in J. Amer. Chem. Soc., 94, 9128 (1972); J. Heterocycl. Chem., 14, 1289 (1977); Tetrahedron Lett., 1977, 5075, etc. in the presence of a catalyst, such as iodine-potassium iodide, N-bromosuccinimide and palladium catalyst.

Manufacturing Process 2

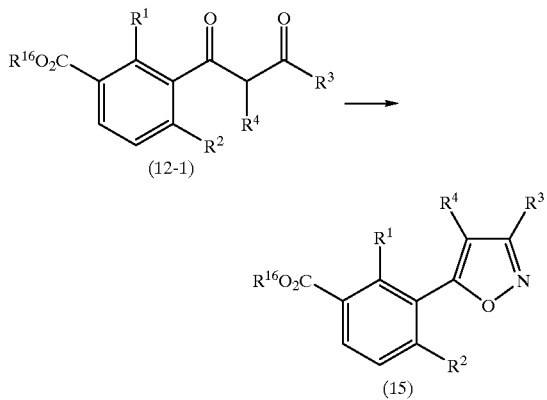

In the process described above, $R^1$, $R^2$, $R^3$, $R^4$ and $R^{16}$ are as defined above.

Alternatively, the isoxazol-form of formula (15) can be manufactured by allowing the diketone-form of formula (12-1) to a reaction with either hydroxylamine or an inorganic salt of hydroxylamine. These reactions described above are proceeded in an appropriate solvent at a temperature of from 0° C. to the boiling point of a solvent used. In this reaction, acids, such as sulfuric acid and p-toluenesulfonic acid, can be used as well. As examples for the solvent, alcohols, such as methanol, ethanol and isopropanol, hydrocarbons, such as benzene and toluene, halogenated hydrocarbons, such as dichloromethane and chloroform, ethers, such as THF and dioxane, nitriles like acetonitrile, DMF, pyridine, acetic acid, water, or the like and mixtures of 2 or more of these examples described above can be given.

Manufacturing Process 3

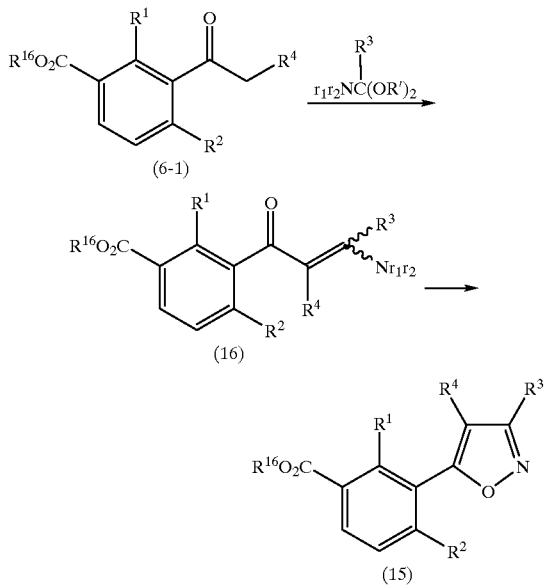

In the process described hereinabove, $R^1$, $R^2$, $R^3$, $R^4$ and $R^{16}$ are as defined above, and $r_1$, $r_2$ and R' each independently represent a lower alkyl.

Whereas, the isoxazol-form of formula (15) can be manufactured by firstly allowing a starting material, the acyl-form of formula (6-1) described above, to a reaction with N,N-dialkylalkylamide dialkylacetal such as N,N-dimethylformamide dimethylacetal to prepare the dialkylaminomethylydene-form of formula (16) and subsequently allowing the said dialkylaminomethylydene-form to a reaction with hydroxylamine.

The first step reaction described above is proceeded in either no solvent system or an inactive solvent, such as benzene, toluene and xylene, at a temperature of from an ambient temperature to the boiling point of a solvent used, or at a temperature of the boiling point of N,N-dialkylalkylamide dialkylacetal when the reaction is proceeded without a solvent. Whereas, the second step reaction described is proceeded by applying either hydroxylamine hydrochloride or hydroxylamine sulfate, both being in an amount of 1.0 to 2.0 times mole relative to 1 mole of the compound of formula (16), to the compound of formula (16) in a solvent, such as ethers including dioxane, ether, tetrahydrofuran and 1,2-dimethoxy ethane, dipolar aprotic solvents including DMF, DMSO, etc. and alcohols including methanol, ethanol, etc. Alternatively, it is also possible to apply free hydroxylamine after transforming the hydroxylamine salt to free hydroxylamine by using an appropriate base. The reaction is proceeded at a temperature of from an ambient temperature to the boiling point of a solvent used. It is also preferable to add an acid catalyst, such as p-toluenesulfonic acid, sulfuric acid and hydrochloric acid, to complete the ring-closing reaction following to the addition of hydroxylamine.

Manufacturing Process 4

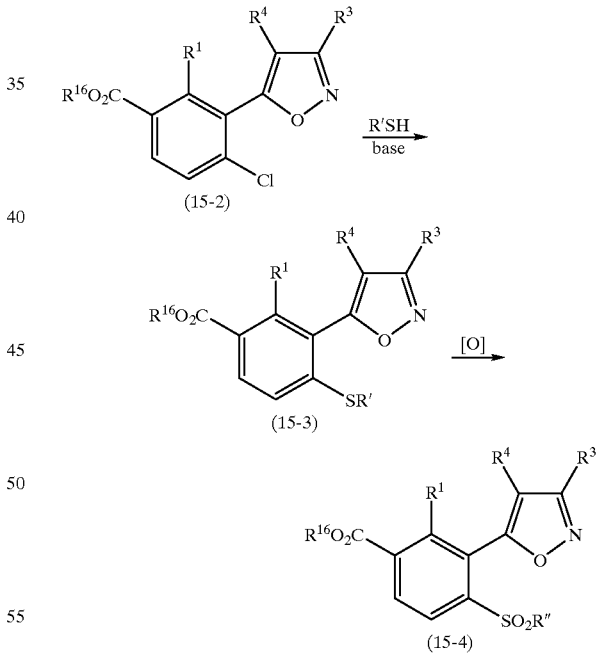

In the process described above, $R^1$, $R^3$, $R^4$ and $R^{16}$ are as defined above, and R" represents a lower alkyl.

Further, benzoic acids represented by a formula (15-4) in the manufacturing process described above can be manufactured by firstly allowing a 4-Cl-type compound of formula (15-2) to a reaction with mercaptan represented by a formula of R'SH in the presence of a base to prepare a 4-SR' type compound of formula (15-3) and subsequently subjecting the 4-SR' type to oxidation process.

As examples for the base to be used in the reaction above, alkali metal hydroxides, such as sodium hydroxide and potassium hydroxide, metal alkoxide, such as sodium methoxide, sodium ethoxide and potassium t-butoxide, carbonates, such as sodium carbonate and potassium carbonate, hydrides like sodium hydride, and organic bases, such as triethylamine, diisopropylethylamine, 1-diazabicyclo[5,4,0]-unde-7-cene (DBU) and pyridine, can be given. And, as examples for the solvent to be used in the reaction, alcohols, such as methanol and ethanol, ethers, such as THF and DME, amides, such as DMF and dimethylacetamide (DMA), DMSO, acetonitrile, benzene, toluene, xylene, and the like can be given.

The subsequent oxidation reaction is proceeded in an inactive solvent, such as water, an organic acid like acetic acid and halogenated hydrocarbon including dichloromethane, chloroform and carbon tetrachloride, in the presence of an oxidizing agent including peroxy acids, such as hydrogen peroxide, peracetic acid, perbenzoic acid and m-chloroperbenzoic acid, and hypochlorites such as sodium hypochlorite.

The reaction is proceeded at a temperature ranging from an ambient temperature to the boiling point of a solvent used.

Manufacturing Process 5

Whereas, the isoxazol-form of formula (15) is also obtainable by employing the process described in WO96/26200 Gazette. The following is the process disclosed in this Gazette.

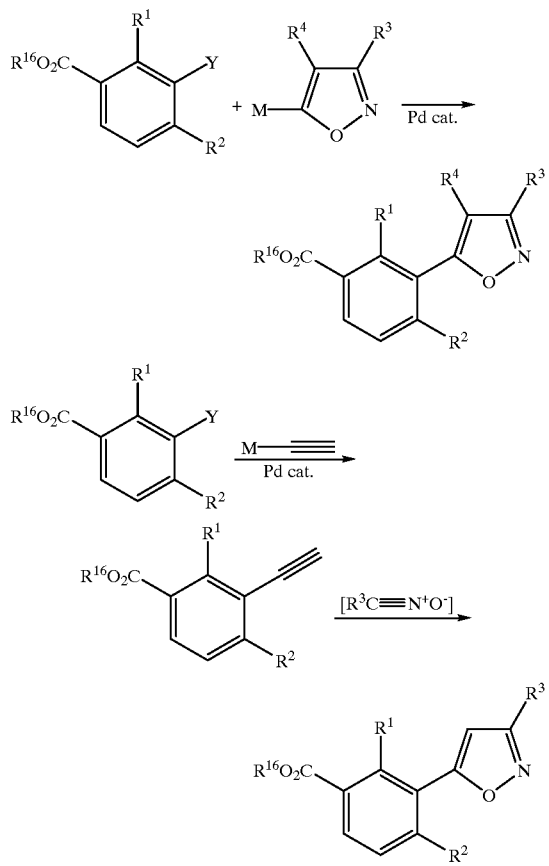

In the process described above, $R^1$, $R^2$, $R^3$ and $R^{16}$ are as defined above, Y represents Br, I or —$OSO_2CF_3$, and M represents $Sn(C_1-C_6\ alkyl)_3$, $B(OH)_2$ or $ZnCl$.

EXAMPLES

Now, the present invention is further described in detail with referring the examples described below.

Example 1

Manufacturing of 2-[2-chloro-3-(3-methyl-1,2-isoxazol-5-yl)-4-methylsulfonylbenzoyl]-cyclohexane-1,3-dione

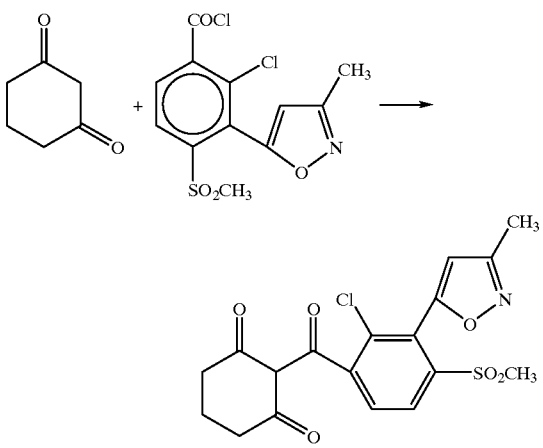

To methylene chloride in an amount of 40 ml, were dissolved 1,3-cyclohexanedione in an amount of 0.60 g and triethylamine in an amount of 0.56 g, and 10 ml methylene chloride solution of 2-chloro-3-(3-methyl-1,2-isoxazol-5-yl)-4-methylsulfonylbenzoyl chloride, which is prepared by allowing 2-chloro-3-(3-methyl-1,2-isoxazol-5-yl)-4-methylsulfonylbenzoic acid in an amount of 1.6 g to a reaction with thionyl chloride in an amount of 3.0 g, was then fed dropwise into the resulting solution at an ambient temperature. After stirring the mixture for 1 hour at an ambient temperature, the reacted-mixture was washed with 1N-hydrochloric acid and then with saturated saline solution, and was dried with anhydrous magnesium sulfate. The solvent remained in the mixture was distillated out under reduced pressure. The residue obtained was dissolved in 40 ml acetonitrile and was stirred over a night at an ambient temperature following to the addition of triethylamine in an amount of 0.56 g and acetone cyanohydrin in an amount of 0.13 g to the solution. After distillating out the solvent remained under reduced pressure, the residue obtained was dissolved in ethyl acetate, washed with diluted hydrochloric acid and saturated saline solution in turn and was then dried with anhydrous magnesium sulfate. The solvent remained in the residue was further distillated out under reduced pressure, and the residue was purified by using silica gel column chromatography (ratio of chloroform to methanol: 98:2) to thereby obtain an objective product in an amount of 0.97 g in crystalline form. The melting point was found to be a range of 166–168° C.

Example 2

Manufacturing of 5-tert-butoxymethyl-2-[2-methyl-3-(3-methyl-1,2-isoxazol-5-yl)-4-methylsulfonylbenzoyl]-cyclohexane-1,3-dione

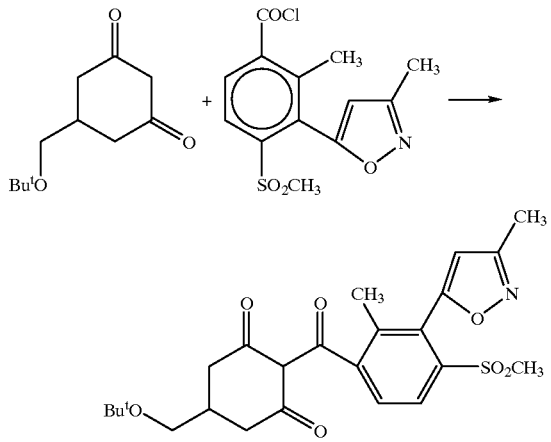

According to a customarily-employed method, 2-methyl-3-(3-methyl-1,2-isoxazol-5-yl)-4-methylsulfonylbenzoyl chloride was prepared by using 2-methyl-3-(3-methyl-1,2-isoxazol-5-yl)-4-methylsulfonylbeiizoic acid in an amount of 1.16 g as a starting material. Then 2-methyl-3-(3-methyl-1,2-isoxazol-5-yl)-4-methylsulfonylbenzoyl chloride obtained and 5-tert-butoxymethyl-cyclohexane-1,3-dione in an amount of 0.71 g were dissolved together in 10 ml chloroform, and triethylamine in an amount of 0.36 g was fed dropwise into the resulting solution under cooling with ice. After stirring the solution for 30 minutes at an ambient temperature, the solution was poured into ice water and acidified with diluted hydrochloric acid. and the chloroform layer resulted was then separated out. The organic layer obtained was washed with water, saturated aqueous solution of sodium hydrogencarbonate and saturated saline solution in series, and then dried with anhydrous magnesium sulfate. The residue obtained by distillating out the solvent remained under reduced pressure was dissolved in 10 ml acetonitrile, then, triethylamine in an amount of 0.41 g and acetone cyanohydrin in an amount of 0.06 g were added in to the resulting solution, and the solution was stirred for 3 days at an ambient temperature. After distillating out the solvent in the solution, the residue obtained was dissolved in ethyl acetate, washed with diluted hydrochloric acid and saturated saline solution in turn, and was dried with anhydrous magnesium sulfate. The residue obtained by distillating out the solvent therein was purified by using a silica gel column chromatography, wherein chloroform was used as a developer, to obtain an objective product in an amount of 0.18 g.

$^1$H-NMR (CDCL$_3$, δ ppm): 1.14 (s, 9H), 2.03 (s, 3H), 2.39 (s, 3H), 2.40 (m, 3H), 2.80 (m, 2H), 2.93 (s, 3H), 3.35 (m, 2H), 6.39 (s, 1H), 7.31 (d, 1H, J=8.2 Hz), 8.07 (d, 1H, J=8.0 Hz), 17.21 (bs, 1H).

Example 3

Manufacturing of 5-hydroxymethyl-2-[2-methyl-3-(3-methyl-1,2-isoxazol-5-yl)-4-methylsulfonylbenzoyl]-cyclohexane-1,3-dione

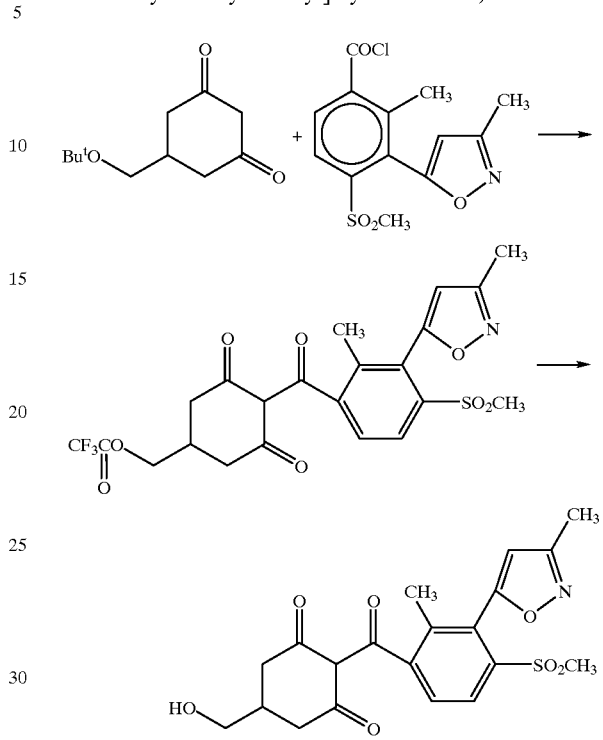

Crude 5-tert-butoxymethyl-2-[2-methyl-3-(3-methyl-1,2-isoxazol-5-yl)-4-methylsulfonylbenzoyl]-cyclohexan-1,3-dione in an amount of 1.51 g obtained in the example 2 was dissolved in 15 ml trifluoroacetic acid and was stirred over a night at an ambient temperature. The reacted-mixture was poured into ice water and extracted with ethyl acetate. The organic layer obtained was washed with water and subsequently with saturated saline solution, then the solvent therein was distillated out under reduced pressure to obtain 2-[2-methyl-3-(3-methyl-1,2-isoxazol-5-yl)-4-methylsulfonylbenzoyl]-5-trifluoroacetoxycyclohexane-1,3-dione. The compound obtained was then dissolved in 10 ml ethanol, and 10 ml aqueous solution containing sodium carbonate in an amount of 1.24 g was added to the ethanol solution obtained above. Then the solution was stirred for 6 hours at an ambient temperature. After distillating out the solvent in the solution, the solution was washed with ethyl acetate after adding water thereto, and the water layer resulted was separated out. The aqueous layer obtained was acidified with diluted hydrochloric acid and was extracted with ethyl acetate. The organic layer obtained was washed with water and subsequently with saturated saline solution and dried with anhydrous magnesium sulfate, and the solvent therein was distillated out under reduced pressure to obtain a residue in an amount of 1.01 g. The crude residual product obtained above in an amount 0.21 g was collected and was purified by using a silica gel column chromatography, wherein chloroform was used as a developer, to obtain an objective product in an amount of 0.09 g in powder form $^1$H-NMR (CDCl$_3$, δ ppm): 2.05 (s, 3H), 2.42 (s, 3H), 2.45 (m, 3H), 2.85 (m, 2H), 2.95 (s, 3H), 3.67 (m, 2H), 6.41 (s, 1H), 7.34 (d, 1H, J=8.3 Hz), 8.10 (d, 1H, J=8.3 Hz), 17.24 (bs, 1H).

Example 4

Manufacturing of 3-[2-methyl-3-(3-methyl-1,2-isoxazol-5-yl)-4-methylsulfonylbenzoyl]-bicyclo[4,1,0]heptane-2,4-dione

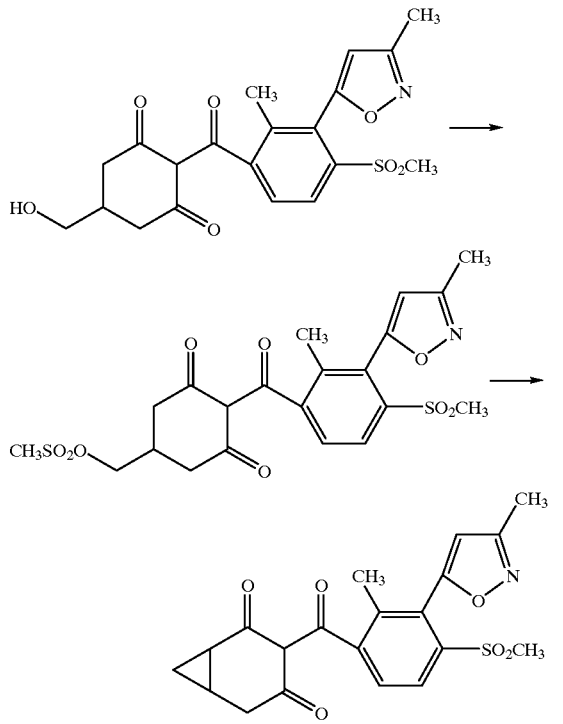

Crude 5-hydroxymethyl-2-[2-methyl-3-(3-methyl-1,2-isoxazol-5-yl)-4-methylsulfonylbenzoyl]-cyclohexane-1,3-dione in an amount of 0.80 g obtained in the example 3 was dissolved in 10 ml chloroform and was then fed dropwise with triethylamine in an amount of 0.58 g under cooling with ice. The mixture was then added with anhydrous methane sulfonate in an amount of 0.40 g and stirred for 1 hour at an ambient temperature. The reacted-mixture was poured into ice water and was separated after acidifying it with diluted hydrochloric acid. The chloroform layer resulted was washed with water and subsequently with saturated saline solution, and then dried with anhydrous magnesium sulfate. After distillating out the solvent remained in the layer under reduced pressure, the crude 5-methylsulfonyloxymethyl-2-[2-methyl-3-(3-methyl-1,2-isoxazol-5-yl)-4-methylsulfonylbenzoyl]-cyclohexane-1,3-dione obtained was dissolved in 10 ml ethanol and was stirred for 6 days at an ambient temperature after adding aqueous solution of 1N-sodium hydroxide in an amount of 5.7 ml. After distillating out the solvent therein under reduced pressure, the residue obtained was added into water, acidified with diluted hydrochloric acid and extracted with ethyl acetate. The organic layer resulted was washed with water and subsequently with saturated saline solution and was dried with anhydrous magnesium sulfate, and the solvent remained in the layer was distillated out under reduced pressure to obtain a residue in an amount of 0.54 g. The residue was purified by using a silica gel column chromatography, wherein chloroform is used as a developer, to obtain an objective product in an amount of 0.35 g in yellowish crystalline form The melting point was found to be in a range of 201–203° C.

Example 5

Manufacturing of 5-hydroxymethyl-4-methyl-2-[2-methyl-4-methylsulfonyl-3-(3-methyl-1,2-isoxazol-5-yl)benzoyl]cyclohexane-1,3-dione

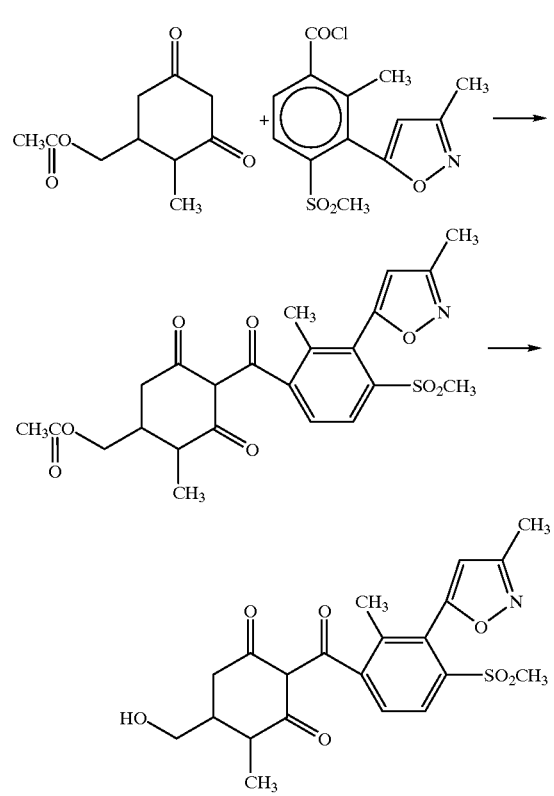

Example 5

To 5 ml methylene chloride, was dissolved 5-acetoxymethyl-4-methylcyclohexane-1,3-dione in an amount of 0.44 g, and to the resulting solution, was fed dropwise 5 ml methylene chloride solution containing 2-methyl-4-methylsulfonyl-3-(3-methyl-1,2-isoxazol-5-yl) benzoyl chloride in an amount of 0.6 g, and the resulting mixture was then stirred for 1 hour at an ambient temperature. The reacted-mixture was then added with water and subsequently with diluted hydrochloric acid to acidify the mixture and was extracted with chloroform. The organic layer obtained was washed with water and subsequently with saturated saline solution and was dried with anhydrous magnesium sulfate. After distillating out the solvent remained in the layer under reduced pressure, the residue obtained was added with 5 ml methanol and 5 ml aqueous solution of 1N-sodium hydroxide and was stirred for 12 hours at an ambient temperature. The reacted-mixture was then added with water and then with diluted hydrochloric acid to acidify the mixture and was extracted with chloroform. The organic layer obtained was washed with water and subsequently with saturated saline solution and was dried with anhydrous magnesium sulfate. The solvent remained in the layer was distillated out under reduced pressure, and the residue obtained was purified by using a silica gel column chromatography to obtain the captioned-compound in an amount of 0.85 g in amorphous form.

Example 6

Manufacturing of 3-[2-methyl-3-(3-methyl-1,2-isoxazol-5-yl)-4-methylsulfonylbenzoyl]-5-methylbicyclo[4,1,0]heptane-2,4-dione (Trans-form)

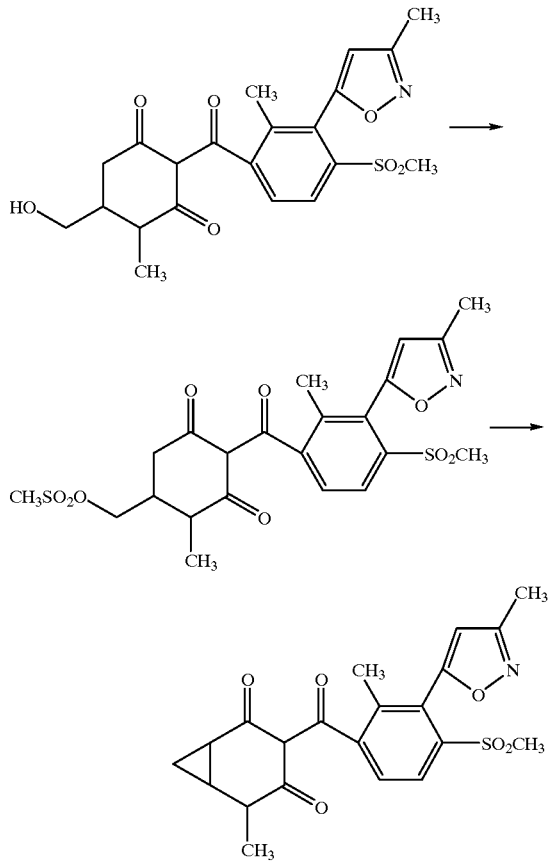

To 5 ml methylene chloride, were dissolved 5-hydroxymethyl-4-methyl-2-[2-methyl-4-methylsulfonyl-3-(3-methyl-1,2-isoxazol-5-yl) benzoyl]cyclohexane-1,3-dione in an amount of 0.4 g and triethylamine in an amount of 0.2 g, and 5 ml methylene chloride solution containing methane sulfonate anhydride in an amount of 0.2 g was fed dropwise into the resulting solution and the solution was stirred for 1 hour at an ambient temperature. The reacted-mixture was then added with water and then with diluted hydrochloric acid to acidify the solution, and the mixture was then extracted with chloroform. The organic layer obtained was washed with water and subsequently with saturated saline solution and was then dried with anhydrous magnesium sulfate. The residue obtained by distillating out the solvent remained in the layer under reduced pressure was added with 5 ml methanol and 5 ml aqueous solution of 1N-sodium hydroxide and was stirred for 4 hours at an ambient temperature. The reacted-mixture was then added with water and then with diluted hydrochloric acid to acidify the mixture. and the mixture was then extracted with chloroform. The organic layer obtained was washed with water and subsequently with saturated saline solution and dried with anhydrous magnesium sulfate, and the solvent remained therein was distillated out under reduced pressure. The residue obtained was collected out and was purified by using a thin layer chromatography to obtain the captioned-compound in an amount of 0.1 g in amorphous form.

The examples for the compounds specified in the present invention, which can be manufactured according to the processes as described above are shown in the following Tables 1 through 5.

TABLE 1

| Compound No. | $R^1$ | $R^2$ | $R^3$ | $R^4$ | Physical* data |
|---|---|---|---|---|---|
| I-1 | Cl | Cl | H | H | |
| I-2 | Cl | $SO_2CH_3$ | H | H | |
| I-3 | Cl | Cl | $CH_3$ | H | powder |
| I-4 | Cl | $SO_2CH_3$ | $CH_3$ | H | [166–168] |
| I-5 | Cl | Cl | H | $CH_3$ | |
| I-6 | Cl | $SO_2CH_3$ | H | $CH_3$ | |
| I-7 | Cl | Cl | $CH_3$ | $CH_3$ | |
| I-8 | Cl | $SO_2CH_3$ | $CH_3$ | $CH_3$ | |
| I-9 | F | Cl | H | H | |
| I-10 | F | $SO_2CH_3$ | H | H | |
| I-11 | F | Cl | $CH_3$ | H | |
| I-12 | F | $SO_2CH_3$ | $CH_3$ | H | |
| I-13 | F | Cl | H | $CH_3$ | |
| I-14 | F | $SO_2CH_3$ | H | $CH_3$ | |
| I-15 | Br | Cl | H | H | |
| I-16 | Br | $SO_2CH_3$ | H | H | |
| I-17 | Br | Cl | $CH_3$ | H | |
| I-18 | Br | $SO_2CH_3$ | $CH_3$ | H | |
| I-19 | Br | Cl | H | $CH_3$ | |
| I-20 | Br | $SO_2CH_3$ | H | $CH_3$ | |
| I-21 | $CH_3$ | Cl | H | H | |
| I-22 | $CH_3$ | $SO_2CH_3$ | H | H | |
| I-23 | $CH_3$ | Cl | $CH_3$ | H | |
| I-24 | $CH_3$ | $SO_2CH_3$ | $CH_3$ | H | |
| I-25 | $CH_3$ | Cl | H | $CH_3$ | |
| I-26 | $CH_3$ | $SO_2CH_3$ | H | $CH_3$ | |
| I-27 | $CH_3$ | Cl | $CH_3$ | $CH_3$ | |
| I-28 | $CH_3$ | $SO_2CH_3$ | $CH_3$ | $CH_3$ | |
| I-29 | $OCH_3$ | Cl | H | H | |
| I-30 | $OCH_3$ | $SO_2CH_3$ | H | H | |
| I-31 | $OCH_3$ | Cl | $CH_3$ | H | |
| I-32 | $OCH_3$ | $SO_2CH_3$ | $CH_3$ | H | |
| I-33 | $OCH_3$ | Cl | H | $CH_3$ | |
| I-34 | $OCH_3$ | $SO_2CH_3$ | H | $CH_3$ | |
| I-35 | $OCF_3$ | Cl | H | H | |
| I-36 | $CF_3$ | $SO_2CH_3$ | H | H | |
| I-37 | $CF_3$ | Cl | $CH_3$ | H | |
| I-38 | $CF_3$ | $SO_2CH_3$ | $CH_3$ | H | |
| I-39 | $CF_3$ | Cl | H | $CH_3$ | |
| I-40 | $CF_3$ | $SO_2CH_3$ | H | $CH_3$ | |

TABLE 2

| Compound No. | $R^1$ | $R^2$ | $R^3$ | $R^4$ | Physical* data |
|---|---|---|---|---|---|
| II-1 | Cl | Cl | H | H | |
| II-2 | Cl | $SO_2CH_3$ | H | H | |

TABLE 2-continued

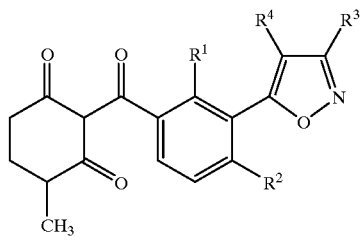

| Compound No. | R¹ | R² | R³ | R⁴ | Physical* data |
|---|---|---|---|---|---|
| II-3 | Cl | Cl | CH₃ | H | powder |
| II-4 | Cl | SO₂CH₃ | CH₃ | H | [178–181] |
| II-5 | Cl | Cl | H | CH₃ | |
| II-6 | Cl | SO₂CH₃ | H | CH₃ | |
| II-7 | Cl | Cl | CH₃ | CH₃ | |
| II-8 | Cl | SO₂CH₃ | CH₃ | CH₃ | |
| II-9 | F | Cl | H | H | |
| II-10 | F | SO₂CH₃ | H | H | |
| II-11 | F | Cl | CH₃ | H | |
| II-12 | F | SO₂CH₃ | CH₃ | H | |
| II-13 | F | Cl | H | CH₃ | |
| II-14 | F | SO₂CH₃ | H | CH₃ | |
| II-15 | Br | Cl | H | H | |
| II-16 | Br | SO₂CH₃ | H | H | |
| II-17 | Br | Cl | CH₃ | H | |
| II-18 | Br | SO₂CH₃ | CH₃ | H | |
| II-19 | Br | Cl | H | CH₃ | |
| II-20 | Br | SO₂CH₃ | H | CH₃ | |
| II-21 | CH₃ | Cl | H | H | |
| II-22 | CH₃ | SO₂CH₃ | H | H | |
| II-23 | CH₃ | Cl | CH₃ | H | |
| II-24 | CH₃ | SO₂CH₃ | CH₃ | H | |
| II-25 | CH₃ | Cl | H | CH₃ | |
| II-26 | CH₃ | SO₂CH₃ | H | CH₃ | |
| II-27 | CH₃ | Cl | CH₃ | CH₃ | |
| II-28 | CH₃ | SO₂CH₃ | CH₃ | CH₃ | |
| II-29 | OCH₃ | Cl | H | H | |
| II-30 | OCH₃ | SO₂CH₃ | H | H | |
| II-31 | OCH₃ | Cl | CH₃ | H | |
| II-32 | OCH₃ | SO₂CH₃ | CH₃ | H | |
| II-33 | OCH₃ | Cl | H | CH₃ | |
| II-34 | OCH₃ | SO₂CH₃ | H | CH₃ | |
| II-35 | OCF₃ | Cl | H | H | |
| II-36 | CF₃ | SO₂CH₃ | H | H | |
| II-37 | CF₃ | Cl | CH₃ | H | |
| II-38 | CF₃ | SO₂CH₃ | CH₃ | H | |
| II-39 | CF₃ | Cl | H | CH₃ | |
| II-40 | CF₃ | SO₂CH₃ | H | CH₃ | |

TABLE 3

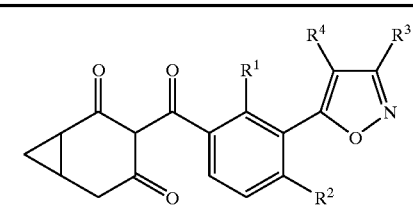

| Compound No. | R¹ | R² | R³ | R⁴ | Physical* data |
|---|---|---|---|---|---|
| III-1 | Cl | Cl | H | H | |
| III-2 | Cl | SO₂CH₃ | H | H | |
| III-3 | Cl | Cl | CH₃ | H | |

TABLE 3-continued

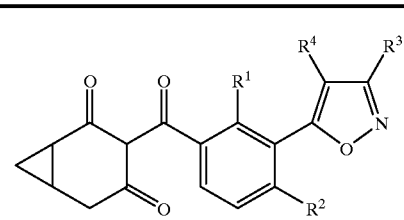

| Compound No. | R¹ | R² | R³ | R⁴ | Physical* data |
|---|---|---|---|---|---|
| III-4 | Cl | SO₂CH₃ | CH₃ | H | powder |
| III-5 | Cl | Cl | H | CH₃ | |
| III-6 | Cl | SO₂CH₃ | H | CH₃ | |
| III-7 | Cl | Cl | CH₃ | CH₃ | |
| III-8 | Cl | SO₂CH₃ | CH₃ | CH₃ | |
| III-9 | F | Cl | H | H | |
| III-10 | F | SO₂CH₃ | H | H | |
| III-11 | F | Cl | CH₃ | H | |
| III-12 | F | SO₂CH₃ | CH₃ | H | |
| III-13 | F | Cl | H | CH₃ | |
| III-14 | F | SO₂CH₃ | H | CH₃ | |
| III-15 | Br | Cl | H | H | |
| III-16 | Br | SO₂CH₃ | H | H | |
| III-17 | Br | Cl | CH₃ | H | |
| III-18 | Br | SO₂CH₃ | CH₃ | H | |
| III-19 | Br | Cl | H | CH₃ | |
| III-20 | Br | SO₂CH₃ | H | CH₃ | |
| III-21 | CH₃ | Cl | H | H | |
| III-22 | CH₃ | SO₂CH₃ | H | H | |
| III-23 | CH₃ | Cl | CH₃ | H | |
| III-24 | CH₃ | SO₂CH₃ | CH₃ | H | [201–203] |
| III-25 | CH₃ | Cl | H | CH₃ | |
| III-26 | CH₃ | SO₂CH₃ | H | CH₃ | |
| III-27 | CH₃ | Cl | CH₃ | CH₃ | |
| III-28 | CH₃ | SO₂CH₃ | CH₃ | CH₃ | |
| III-29 | OCH₃ | Cl | H | H | |
| III-30 | OCH₃ | SO₂CH₃ | H | H | |
| III-31 | OCH₃ | Cl | CH₃ | H | |
| III-32 | OCH₃ | SO₂CH₃ | CH₃ | H | [183–186] |
| III-33 | OCH₃ | Cl | H | CH₃ | |
| III-34 | OCH₃ | SO₂CH₃ | H | CH₃ | |
| III-35 | OCF₃ | Cl | H | H | |
| III-36 | CF₃ | SO₂CH₃ | H | H | |
| III-37 | CF₃ | Cl | CH₃ | H | |
| III-38 | CF₃ | SO₂CH₃ | CH₃ | H | |
| III-39 | CF₃ | Cl | H | CH₃ | |
| III-40 | CF₃ | SO₂CH₃ | H | CH₃ | |

TABLE 4

| Compound No. | R¹ | R² | R³ | R⁴ | R⁹ | Configuration | Physical* data |
|---|---|---|---|---|---|---|---|
| IV-1 | Cl | Cl | H | H | H | cis | |
| IV-2 | Cl | Cl | H | H | H | trans | |
| IV-3 | Cl | SO₂CH₃ | H | H | H | cis | |
| IV-4 | Cl | SO₂CH₃ | H | H | H | trans | |
| IV-5 | Cl | Cl | CH₃ | H | H | cis | |
| IV-6 | Cl | Cl | CH₃ | H | H | trans | powder |
| IV-7 | Cl | SO₂CH₃ | CH₃ | H | H | cis | powder |
| IV-8 | Cl | SO₂CH₃ | CH₃ | H | H | trans | [166–169] |
| IV-9 | Cl | SO₂CH₃ | CH₃ | H | CO₂Et | cis | |
| IV-10 | Cl | SO₂CH₃ | CH₃ | H | CO₂Et | trans | powder |
| IV-11 | Cl | SO₂CH₃ | CH₃ | H | OH | cis | |
| IV-12 | Cl | SO₂CH₃ | CH₃ | H | OH | trans | |
| IV-13 | Cl | SO₂CH₃ | CH₃ | H | OC₃H₇ | cis | powder |
| IV-14 | Cl | SO₂CH₃ | CH₃ | H | OC₃H₇ | trans | powder |
| IV-15 | CH₃ | Cl | H | H | H | cis | |
| IV-16 | CH₃ | Cl | H | H | H | trans | |
| IV-17 | CH₃ | SO₂CH₃ | H | H | H | cis | |
| IV-18 | CH₃ | SO₂CH₃ | H | H | H | trans | |
| IV-19 | CH₃ | Cl | CH₃ | H | H | cis | |
| IV-20 | CH₃ | Cl | CH₃ | H | H | trans | |
| IV-21 | CH₃ | SO₂CH₃ | CH₃ | H | H | cis | |
| IV-22 | CH₃ | SO₂CH₃ | CH₃ | H | H | trans | powder |
| IV-23 | CH₃ | SO₂CH₃ | CH₃ | H | H | cis | |
| IV-24 | CH₃ | SO₂CH₃ | CH₃ | H | H | trans | |
| IV-25 | CH₃ | SO₂CH₃ | CH₃ | H | H | cis | |
| IV-26 | CH₃ | SO₂CH₃ | CH₃ | H | H | trans | |
| IV-27 | CH₃ | SO₂CH₃ | CH₃ | H | H | cis | |
| IV-28 | CH₃ | SO₂CH₃ | CH₃ | H | H | trans | |
| IV-29 | OCH₃ | Cl | H | H | H | cis | |
| IV-30 | OCH₃ | Cl | H | H | H | trans | |
| IV-31 | OCH₃ | SO₂CH₃ | H | H | H | cis | |
| IV-32 | OCH₃ | SO₂CH₃ | H | H | H | trans | |
| IV-33 | OCH₃ | Cl | CH₃ | H | H | cis | |
| IV-34 | OCH₃ | Cl | CH₃ | H | H | trans | |
| IV-35 | OCH₃ | SO₂CH₃ | CH₃ | H | H | cis | |
| IV-36 | OCH₃ | SO₂CH₃ | CH₃ | H | H | trans | |
| IV-37 | OCH₃ | SO₂CH₃ | CH₃ | H | CO₂Et | cis | |
| IV-38 | OCH₃ | SO₂CH₃ | CH₃ | H | CO₂Et | trans | |
| IV-39 | OCH₃ | SO₂CH₃ | CH₃ | H | OH | cis | |
| IV-40 | OCH₃ | SO₂CH₃ | CH₃ | H | OH | trans | |
| V-41 | OCH₃ | SO₂CH₃ | CH₃ | H | OC₃H₇ | cis | |
| V-42 | OCH₃ | SO₂CH₃ | CH₃ | H | OC₃H₇ | trans | |

TABLE 5

| Compound No. | R¹ | R² | R⁵ | R⁶ | R⁷ | R⁸ | R⁹ | R¹⁰ | Physical data |
|---|---|---|---|---|---|---|---|---|---|
| V-1 | Cl | Cl | H | H | CH₃ | CH₃ | H | H | |
| V-2 | Cl | SO₂CH₃ | H | H | CH₃ | CH₃ | H | H | |
| V-3 | Cl | Cl | CH₃ | CH₃ | H | CH₃ | H | H | |
| V-4 | Cl | SO₂CH₃ | CH₃ | CH₃ | H | CH₃ | H | H | powder |

TABLE 5-continued

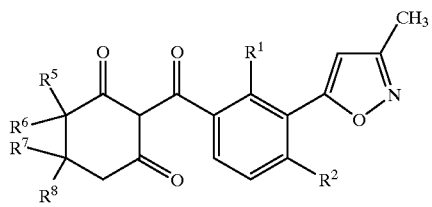

| Compound No. | $R^1$ | $R^2$ | $R^5$ | $R^6$ | $R^7$ | $R^8$ | $R^9$ | $R^{10}$ | Physical data |
|---|---|---|---|---|---|---|---|---|---|
| V-5 | Cl | Cl | H | H | H | $CH_2OCH_3$ | H | H | |
| V-6 | Cl | $SO_2CH_3$ | H | H | H | $CH_2OCH_3$ | H | H | powder |
| V-7 | Cl | Cl | H | H | H | $CH_2OCOCH_3$ | H | H | |
| V-8 | Cl | $SO_2CH_3$ | H | H | H | $CH_2OCOCH_3$ | H | H | powder |
| V-9 | Cl | Cl | H | H | H | $CH_2OH$ | H | H | |
| V-10 | Cl | $SO_2CH_3$ | H | H | H | $CH_2OH$ | H | H | powder |
| V-11 | Cl | Cl | H | H | H | $CH_2CH(CH_3)SEt$ | H | H | |
| V-12 | Cl | $SO_2CH_3$ | H | H | H | $CH_2CH(CH_3)SEt$ | H | H | powder |
| V-13 | Cl | Cl | $CH_3$ | H | H | $CH_2OCH_3$ | H | H | |
| V-14 | Cl | $SO_2CH_3$ | $CH_3$ | H | H | $CH_2OCH_3$ | H | H | powder |
| V-15 | Cl | Cl | $CH_3$ | H | H | $CH_2OCOCH_3$ | H | H | |
| V-16 | Cl | $SO_2CH_3$ | $CH_3$ | H | H | $CH_2OCOCH_3$ | H | H | powder |
| V-17 | Cl | Cl | $CH_3$ | H | H | $CH_2OH$ | H | H | powder |
| V-18 | Cl | $SO_2CH_3$ | $CH_3$ | H | H | $CH_2OH$ | H | H | powder |
| V-19 | Cl | Cl | $SCH_3$ | $CH_3$ | $CH_3$ | H | H | H | |
| V-20 | Cl | $SO_2CH_3$ | $SCH_3$ | $CH_3$ | $CH_3$ | H | H | H | powder |
| V-21 | Cl | Cl | $CH_3$ | $CH_3$ | =CO | | $CH_3$ | $CH_3$ | |
| V-22 | Cl | $SO_2CH_3$ | $CH_3$ | $CH_3$ | =CO | | $CH_3$ | $CH_3$ | powder |
| V-23 | $CH_3$ | $SO_2CH_3$ | H | H | H | $CH_2OBu^t$ | H | H | powder |
| V-24 | $CH_3$ | Cl | H | H | H | $CH_2OH$ | H | H | |
| V-25 | $CH_3$ | $SO_2CH_3$ | H | H | H | $CH_2OH$ | H | H | powder |
| V-26 | $OCH_3$ | Cl | H | H | H | $CH_2OH$ | H | H | |
| V-27 | $OCH_3$ | $SO_2CH_3$ | H | H | H | $CH_2OH$ | H | H | |

$^1$H-NMR data(δ ppm) for the compounds described in Tables 1 through 5 are shown in Table 6.

TABLE 6

| Compound No. | $^1$H-NMR data (δ ppm) |
|---|---|
| I-3 | 2.04 (m, 2H), 2.40 (s, 3H), 2.43 (m, 2H), 2.78 (m, 2H), 6.32 (s, 1H), 7.25 (m, 1H), 7.47 (m, 1H), 16.68 (s, 1H) |
| II-3 | 1.12, 1.40 (d, 3H), 1.82 (m, 1H), 1.82 (m, 1H), 2.13 (m, 1H), 2.45 (m, 5H), 2.82 (m, 1H), 6.33 (s, 1H), 7.25 (m, 1H), 7.47 (m, 1H) |
| II-4 | 1.12, 1.40 (d, 3H), 1.60 (s, 3H), 1.82 (m, 1H), 2.13 (m, 1H), 2.41 (s, 3H), 2.36–2.58 (m, 2H), 2.85 (m, 1H), 3.06 (s, 3H) |
| III-4 | 0.80–1.02 (m, 1H), 1.38 (m, 1H), 1.66–2.21 (m, 2H), 2.41 (s, 3H), 2.70–2.88 (m, 1H), 3.01–3.22 (m, 1H), 3.06 (s, 3H), 6.47 (m, 1H), 7.52 (m, 1H), 8.20 (m, 1H), 16.26, 17.01 (s, 1H) |
| IV-6 | 0.81, 1.00 (m, 1H), 1.11–1.38 (m, 1H), 1.29, 1.46 (d, 3H), 1.53–2.20 (m, 2H), 2.39 (s, 3H), 3.10 (m, 1H), 6.31 (s, 1H), 7.22 (m, 1H), 7.46 (m, 1H), 16.33, 17.28 (s, 1H) |
| IV-7 | 0.70, 0.93 (m, 1H), 1.2–2.1 (m, 2H), 1.25 (m, 3H), 1.49, 1.73 (s, 1H), 2.32 (m, 1H), 2.43 (s, 3H), 3.07 (s, 3H) <4.18 (m, 2H), 6.49 (s, 1H), 7.44 (m, 1H), 8.17, 8.24 (d, 1H) |
| IV-8 | 0.83, 0.98 (m, 1H), 1.21–1.41 (m, 1H), 1.29, 1.49 (d, 3H), 1.55–1.73 (m, 1H), 1.85–2.20 (m, 1H), 2.42 (s, 3H), 2.80, 3.13 (m, 1H), 3.07 (s, 3H), 6.48 (m, 1H), 7.53 (m, 1H), 8.22 (m, 1H) |
| IV-10 | 0.76, 0.93 (m, 1H), 1.2–2.1 (m, 2H), 1.25 (m, 3H), 1.49, 1.73 (s, 1H), 2.32 (m, 1H), 2.43 (s, 3H), 3.07 (s, 3H), 4.18 (m, 2H), 6.49 (s, 1H), 7.44 (m, 1H), 8.17, 8.24 (d, 1H) |
| IV-13 | 0.88, 0.98 (t, 3H), 1.12, 1.27 (m, 1H), 1.50, 1.62 (s, 3H), 1.50–2.28 (m, 5H), 2.41 (s, 3H), 3.06 (s, 3H), 3.30–3.81 (m, 2H), 6.48 (m, 1H), 7.55 (m, 1H), 8.20 (m, 1H), 16.78, 17.10 (s, 1H) |
| IV-14 | 0.85 (m, 4H), 1.39, 1.57 (s, 3H), 1.40–1.70 (m, 2H), 1.86–2.08 (m, 1H), 2.15–2.29 (m, 2H), 2.42 (s, 3H), 2.95, 3.37 (m, 1H), 3.08 (s, 3H), 6.49 (s, 1H), 7.56 (m, 1H), 8.20 (m, 1H), 16.45, 17.18 (s, 1H) |
| IV-22 | 0.82, 0.97 (m, 1H), 1.27, 1.48 (d, 3H), 1.20–1.45 (m, 1H), 1.60–2.20 (m, 2H), 2.04, 2.07 (s, 3H), 2.40 (s, 3H), 2.80, 3.13 (m, 1H), 2.94 (s, 3H), 6.48, 6.50 (s, 1H), 7.28–7.38 (m, 1H), 8.06–8.12 (m, 1H), 16.73, 17.50 (bs, 1H) |
| V-4 | 0.98–1.40 (m, 9H), 2.05 (m, 1H), 2.40 (s, 3H), 2.54–2.88 (m, 2H), 3.07 (s, 3H), 6.48 (s, 3H), 7.45 (m, 1H), 8.20 (m, 1H), 16.38, 17.21 (s, 1H) |
| V-6 | 1.62 (m, 1H), 2.42 (s, 3H), 2.47 (m, 2H), 2.85 (m, 2H), 3.07 (s, 3H), 3.34 (s, 3H), 3.37 (m, 2H), 6.48 (s, 3H), 7.43 (m, 1H), 8.20 (m, 1H), 16.60 (s, 3H) |
| V-8 | 2.08 (s, 3H), 2.41 (s, 3H), 2.25–2.95 (m, 5H), 3.07 (s, 3H), 4.08 (m, 2H), 6.48 (s, 1H), 7.45 (m, 1H), 8.20 (m, 1H), 16.60 (s, 1H) |
| V-10 | 2.31–2.52 (m, 3H), 2.40 (s, 3H), 2.85 (m, 2H), 3.06 (s, 3H), 3.62 (m, 2H), 6.48 (s, 1H), 7.45 (m, 1H), 8.20 (m, 1H), 16.60 (s, 1H) |
| V-12 | 1.20–1.33 (m, 6H), 1.60 (m, 3H), 2.18 (m, 2H), 2.40 (s, 3H), 2.55 (m, 5H), 2.82 (m, 2H), 3.05 (s, 3H), 6.48 (s, 1H), 7.42 (m, 1H), 8.20 (m, 1H), 16.58 (s, 1H) |
| V-14 | 1.13, 1.33 (d, 3H), 1.70 (m, 1H), 2.08 (m, 1H), 2.42 (s, 3H), 2.50 (m, 1H), 2.92 (m, 1H), 3.08 (s, 3H), 3.30–3.50 (m, 5H), 6.48 (s, 1H), 7.45 (m, 1H), 8.20 (m, 1H), 16.48, 17.05 (s, 1H) |
| V-16 | 1.10–1.48 (m, 3H), 2.07 (m, 3H), 2.21 (m, 1H), 2.40 (m, 1H), 2.42 (s, 3H), 2.64 (m, 1H), 2.85 (m, 1H), 3.07 (s, 3H), 4.14 (m, 2H), 6.46 (s, 1H), 7.45 (m, 1H), 8.20 (m, 1H) |

TABLE 6-continued

| Compound No. | $^1$H-NMR data (δ ppm) |
|---|---|
| V-17 | 1.10–1.48 (m, 3H), 2.05 (m, 2H), 2.40 (s, 3H), 2.51 (m, 1H), 2.91 (m, 1H), 3.73 (m, 2H), 6.30 (s, 1H), 7.20 (m, 1H), 7.45 (m, 1H) |
| V-18 | 1.05–1.48 (m, 3H), 2.05 (m, 2H), 2.41 (s, 3H), 2.51 (m, 1H), 2.91 (m, 1H), 3.05 (s, 3H), 3.73 (m, 2H), 6.47 (s, 1H), 7.45 (m, 1H), 8.18 (m, 1H) |
| V-20 | 1.22 (m, 3H), 2.03, 2.05 (s, 3H), 2.35–2.81 (m, 2H), 2.42 (s, 3H), 3.07 (s, 3H), 2.99–3.47 (m, 2H), 6.47 (s, 1H), 7.46 (m, 1H), 8.20 (m, 1H), 16.60, 16.72 (s, 1H) |
| V-22 | 1.32 (s, 6H), 1.57 (s, 6H), 2.41 (s, 3H), 3.08 (s, 3H), 6.49 (s, 3H), 7.51 (m, 1H), 8.22 (m, 1H), 17.05 (s, 1H) |
| V-23 | Described in Example 2 |
| V-24 | Described in Example 3 |

REFERENCE EXAMPLES

Reference Example 1

Manufacturing of methyl 2,4-dichloro-3-formylbenzoate

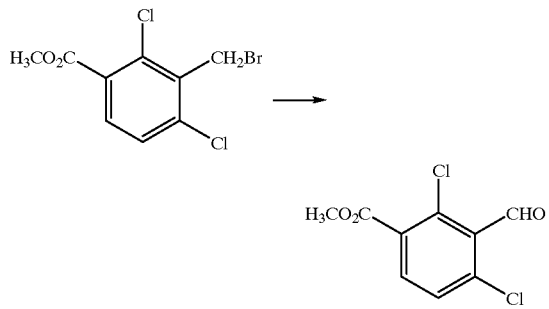

28% methanol solution of sodium methylate in an amount of 26.61 g was added to 100 ml methanol, and to the resulting solution, 2-nitropropane in an amount of 12.29 g was fed dropwise at a temperature lower than 25° C. under cooling with ice. Then, the mixture was added with methyl-3-bromomethyl-2,4-dichlorobenzoate in an amount of 41.16 g and subsequently stirred for 30 minutes under reflux while heating. The reacted-mixture was then cooled and further condensed under reduced pressure, and the residue resulted was dissolved in 1,000 ml ethyl acetate and then washed with 1% aqueous solution of sodium hydroxide under cooling with ice. The organic layer resulted was washed with water and subsequently with saturated saline solution and dried with anhydrous magnesium sulfate. The crystals obtained after distillating out the solvent remained therein under reduced pressure was then washed with benzene and subsequently with n-hexane to obtain an objective compound, 2,4-dichloro-3-formylbenzoate in an amount of 22.00 g in crystalline form. The melting point of the compound was found to be in a range of 103–104° C.

Reference Example 2

Manufacturing of 2,4-dichloro-3-formylbenzoic acid

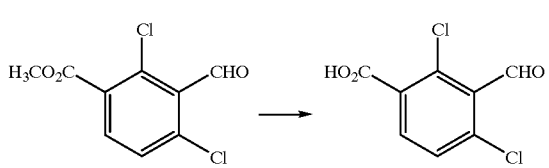

To 5 ml ethanol, was dissolved 2,4-dichloro-3-formylbenzoate in an amount of 1.04 g, and the resulting solution was then added with 10 ml aqueous solution of 1N-sodium hydroxide and further stirred for 17 hours at an ambient temperature. The reacted-mixture was poured into 40 ml ice water and then acidified with concentrated hydrochloric acid, and the crystals resulted were filtrated and then dried to obtain an objective product, 2,4-dichloro-3-formylbenzoic acid in an amount of 0.75 g in crystalline form. The melting point of the product was found to be in a range of 188–190° C.

Reference Example 3

Manufacturing of 2,4-dichloro-3-(3-methyl-1,2-isoxazol-5-yl)benzoic acid

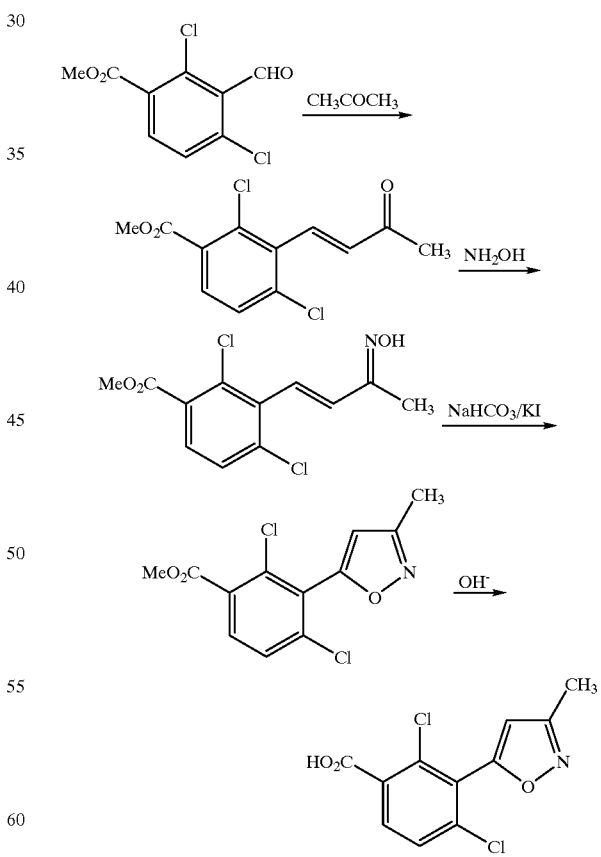

To a mixed solvent composed of 120 ml acetone and 12 ml water, was dissolved 3-formyl-2,4-dichlorobenzoate in an amount of 24.7 g (0.1 mole), and the resulting solution was then cooled with ice water, fed dropwise with 35 ml aqueous solution of 1N-sodium hydroxide at a temperature lower than 20° C. and further stirred over a night at an ambient temperature. The reacted-mixture was poured into ice water, acidified with concentrated hydrochloric acid and then extracted with ethyl acetate. The ethyl acetate layer resulted was washed with saturated saline solution, dried with anhydrous magnesium sulfate and then condensed under reduced pressure. The residue resulted was dissolved in benzene and then subjected to a reflux for 4 hours under heating while removing water therein following to the addition of p-toluenesulfonic acid in a catalystic amount. After cooling, the residue solution was then washed with saturated saline solution, dried with anhydrous magnesium sulfate and further condensed under reduced pressure. The residue obtained was then purified by using a silica gel column chromatography to obtain methyl 2,4-dichloro-3-(3-oxo-1-butenyl) benzoate in an amount of 15.4 g. The yield was 54.8%.

The obtained methyl 3-(3-oxo-1-butenyl)-2,4-dichlorobenzoate in an amount of 15.4 g (0.056 mole) and hydroxylamine hydrochloride in an amount of 15 g (0.216 mole) were dissolved in a mixed solvent composed of 80 ml ethanol and 80 ml pyridine, and the resulting solution was subjected to a reflux for 2 hours under heating. The reacted solution was then poured into ice water and subsequently extracted with ethyl acetate. The ethyl acetate layer resulted was then washed with 1N-hydrochloric acid solution and subsequently with saturated saline solution and dried with anhydrous magnesium sulfate, and the solvent remained therein was distilled out under reduced pressure to obtain 2, 4-dichloro-3-(3-hydroxyimino-1-butenyl)benzoate in an amount of 15.9 g. The yield was 98.2%.

The obtained 2,4-dichloro-3-(3-hydroxyimino-1-butenyl) benzoate in an amount of 15.9 g (0.052 mole) was dissolved in 250 ml tetrahydrofuran, and to the resulting solution, was added 160 ml aqueous solution containing sodium hydrogencarbonate in an amount of 16.8 g (0.2 mole) and subsequently 120 ml of an aqueous solution containing both potassium iodide in an amount of 30.1 g (0.18 mole) and iodine in an amount of 14 g (0.055 mole), and the resulting mixture was then subjected to a reflux for 4 hours under heating while intercepting light. The reacted-mixture was then poured into ice water and extracted with ethyl acetate after the addition of sodium hydrogensulfite into the mixture. The organic layer resulted was washed with saturated saline solution and dried with anhydrous magnesium sulfate, and the solvent remained in the layer was distilled out under reduced pressure. The residue obtained was purified by using a silica gel column chromatography to obtain methyl 2,4-dichloro-3-(3-methyl-1,2-isoxazol-5-yl) benzoate in an amount of 8.8 g. The yield was 54.5%, and the melting point of the product was found to be in a range of 84–89° C.

The obtained 2,4-dichloro-3-(3-methyl-1,2-isoxazol-5-yl) benzoate in an amount of 2.0 g (0.0069 mole) was dissolved in 21 ml ethyl alcohol, and the resulting solution was then added with aqueous solution of 1N-sodium hydroxide and further stirred over a night at an ambient temperature. The reacted-mixture was poured into ice water and acidified with concentrated hydrochloric acid, and the crystals precipitated were filtrated, washed with water and then dried to obtain 2,4-dichloro-3-(3-methyl-1,2-oxazol-5-yl)benzoic acid in an amount of 1.86 g. The yield was 97.9% and the melting point of the product was found to be in a range of 154–156° C.

Reference Example 4

Manufacturing of 2-chloro-4-methanesulfonyl-3-(3-methyl-1,2-isoxazol-5-yl)benzoic acid

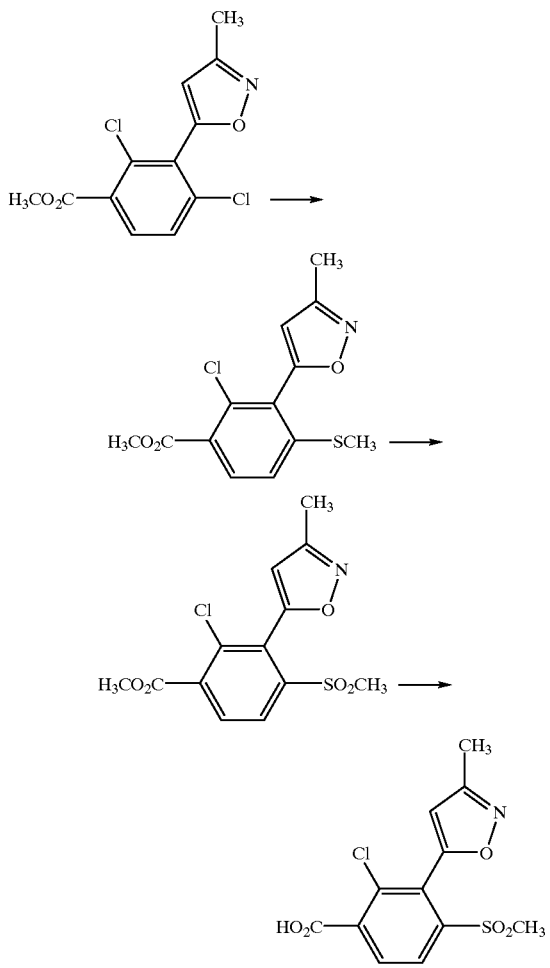

To 20 ml N,N-dimethylformamide, were dissolved 2,4-dichloro-3-( 3-methyl-1,2-isoxazol-5-yl)benzoate in an amount of 8.8 g (0.030 mole) and potassium carbonate in an amount of 4.2 g (0.030 mole), and the resulting solution was then added with methane thiol in an amount of 1.9 g (0.038 mole) and further with 10 ml N,N-dimethylformamide and was further stirred over a night at an ambient temperature. The reacted-mixture was poured into ice water, extracted with ethyl acetate, washed with saturated saline solution and then dried with anhydrous magnesium sulfate, and the solvent remained in the mixture was distilled out under reduced pressure. The residue resulted was purified by using a silica gel column chromatography to obtain methyl 2-chloro-3-(3-methyl-1,2-isoxazol-5-yl)-4-methylthiobenzoate in an amount of 7.49 g. The yield was 82%.

The obtained methyl 2-chloro-3-(3-methyl-1,2-isoxazol-5-yl)-4-methylthiobenzoate in an amount of 7.49 g (0.025 mole) was dissolved in 30 ml chloroform and was then stirred for 3 hours at an ambient temperature following to the addition of m-chloroperbenzoic acid in an amount of 13 g (0.074 mole). The reacted-mixture was then filtrated, and the filtrate obtained was washed with aqueous solution of 1N-sodium hydroxide and subsequently with saturated saline solution and then dried with anhydrous magnesium sulfate, and the solvent remained in the filtrate was distillated out under reduced pressure. The residue resulted was purified by using a silica gel column chromatography to obtain methyl 3-(3-methyl-1,2-isoxazol-5-yl)-2-chloro-4-methanesulfonylbenzoate in an amount of 8.19 g. The yield was 99% and the melting point of the product was found to be in a range of 138–139° C.

The obtained methyl 2-chloro-4-methanesulfonyl-3-(3-methyl-1,2-isoxazol-5-yl)benzoate in an amount of 8.19 g (0.024 mole) was dissolved in 75 ml ethanol, and the resulting solution was then stirred over a night at an ambient temperature following to the addition of aqueous solution of 1N-sodium hydroxide in an amount of 75 ml. The reacted-mixture was poured into ice water and was acidified with concentrated hydrochloric acid, and the crystals precipitated were filtrated, washed with water and dried to obtain an objective product in an amount of 7.49 g in whitish crystalline form. The yield was 96% and the melting point of the product was found to be in a range of 225–228° C.

Reference Example 5

Manufacturing of methyl 3-acetyl-2,4-dichlorobenzoate

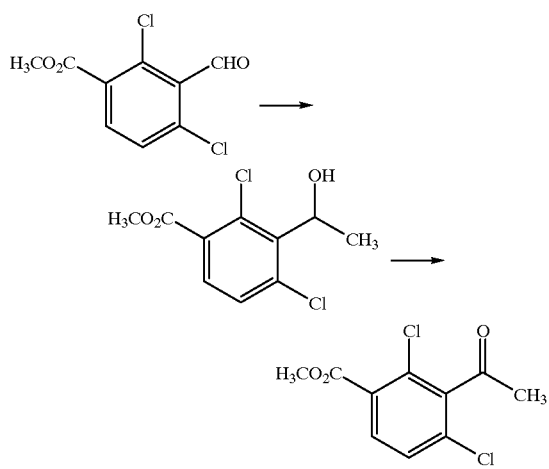

To 20 ml dried-THF, was dissolved 2,4-dichloro-3-formylbenzoate in an amount of 2.47 g, and the resulting solution was then fed dropwise with 4 ml diethyl ether solution of methyl magnesium bromide (3.0 mol/l) at −70° C. After the dropping, the mixture was taken out of a cooling bath and was stirred for 1 hour while raising the temperature of the mixture under natural condition. The reacted-mixture was poured into ice water, acidified with diluted hydrochloric acid and then extracted with diethyl ether. The organic layer resulted was washed with water and saturated saline solution in turn and dried with anhydrous magnesium sulfate. The solvent remained in the layer was concentrated under reduced pressure to obtain methyl 2,4-dichloro-3-(1-hydroxyethyl) benzoate in an amount of 2.42 g as oily substance. Then, 2,4-dichloro-3-(1-hydroxyethyl)benzoate in an amount of 2.42 g was dissolved in 10 ml benzene, and the resulting solution was added with manganese dioxide in an amount of 4 g and further stirred for 1 hour under reflux while heating. The mixture was then further added with manganese dioxide in an amount of 3 g and was stirred for 1 hour under reflux while heating.

The reacted-mixture was cooled down to a room temperature, and insoluble materials therein were separated by filtration. Then, the solvent in the filtrate was distillated out under reduced pressure to obtain an objective product, methyl 3-acetyl-2,4-dichlorobenzoate in an amount of 1.75 g. $n_D^{23}$ 1.5495.

Reference Example 6

Manufacturing of methyl 2,4-dichloro-3-(2-oxopropylbenzoate)

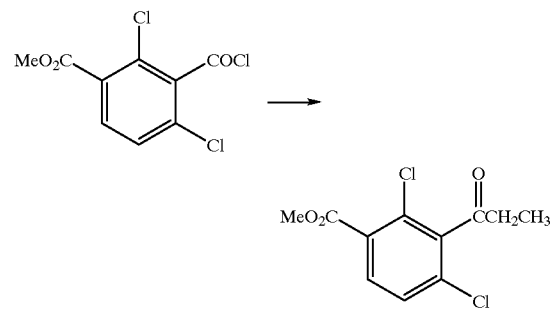

To 100 ml toluene, was added 2,4-dichloro-3-formylbenzoate in an amount of 25.72 g, and the resulting mixture was then added with nitroethane in an amount of 39.0 g and n-butylamine in an amount of 1.5 g and was allowed to a reaction for 21 hours under reflux. The reacted-mixture was poured into ice water, and the mixture was then extracted with ethyl acetate, then the ethyl acetate layer was washed with 1N-hydrochloric acid solution and saturated saline solution in turn and dried with anhydrous magnesium sulfate. The solvent in the layer was distillated out under reduced pressure to obtain methyl 2,4-dichloro-3-(2-nitro-1-propenyl)benzoate in an amount of 34.9 g. The obtained-product in an amount of 30.1 g was then added into a mixed-solvent composed of 120 ml toluene and 360 ml water without taking a purification process for it, and the resulting mixture was fed dropwise with concentrated sulfuric acid in an amount of 104 g at 80° C. following to the addition of both iron powder in an amount of 20.8 g and ferric chloride in an amount of 0.4 g. After the dropping, the mixture was allowed to a reaction for 1 hour under reflux. The reacted-mixture was then allowed to cooling and added with ethyl acetate, and insoluble materials therein were separated by filtration. The organic layer obtained was washed with water and saturated saline solution in turn and dried with anhydrous magnesium sulfate. The solvent in layer was concentrated under reduced pressure, and the residue obtained was purified by using a silica gel column chromatography to obtain 2,4-dichloro-3-(2-oxopropyl) benzoate in an amount of 19.53 g. $n_D^{22}$ 1.5537.

Reference Example 7

Manufacturing of methyl 2,4-dichloro-3-(2-dimethylaminomethylidene-1-oxopropyl)benzoate

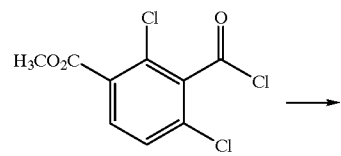

-continued

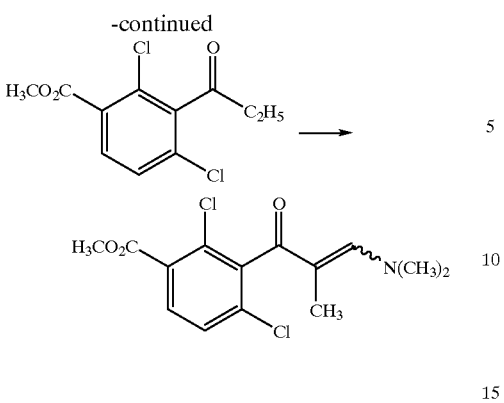

To 150 ml toluene, was dissolved methyl malonate dimethyl ester in an amount of 13.32 g, and the resulting solution was then added with magnesium ethylate in an amount of 10.43 g and further allowed to under reflux for 2 hours while heating. The reacted-mixture was then allowed to cooling and condensed under reduced pressure, and the residue obtained was dissolved in 200 ml toluene. Then, 3-methoxycarbonyl-2,6-dichlorobenzoyl chloride in an amount of 24.40 g was added to the solution, and the resulting mixture was then allowed to under reflux for hour at an ambient temperature and further for 4.5 hours with heating. The reacted-mixture was poured into ice water and acidified with concentrated hydrochloric acid to separate an organic layer. The organic layer obtained was then washed with saturated saline solution and dried with anhydrous magnesium sulfate, and the solvent remained therein was distillated out under reduced pressure to obtain methyl 2,4-dichloro-3-(2,2)-dimethoxycarbonyl-1-oxopropyl)benzoate in an amount of 34.3 g.

The obtained-product was then added into a mixture composed of 40 ml water, diluted sulfuric acid prepared with 8 ml concentrated sulfuric acid and 63 ml acetic acid and was then allowed to under reflux while heating for 12.5 hours. The reacted-mixture was poured into ice water and extracted with ethyl acetate. The organic layer obtained was then washed with water and saturated saline solution in turn and then dried with anhydrous magnesium sulfate. After distillating out the solvent remaining in the layer, carboxylate partly generated was esterificated with methyl iodide in the presence of potassium carbonate according to a customarily-employed method to obtain methyl 2,4-dichloro-3-(1-oxopropyl)benzoate in an amount of 19.31 g.

The obtained-product in an amount of 14.29 g was added into 60 ml N, N-dimethylformamide dimethylacetal, and the resulting mixture was allowed to under reflux and heating for 23.5 hours. After cooling the reacted-mixture down to a room temperature, the residue obtained by condensation under reduced pressure was purified by using a silica gel column chromatography to obtain an objective product, 2,4-dichloro-3-(2-oxo-1-dimethylaminomethylydenepropyl)benzoate in an amount of 7.75 g.

The melting point of the product was found to be in a range of 127.5–128° C.

Reference Example 8

Manufacturing of methyl 2,4-dichloro-3-(4-methylisoxazol-5-yl)benzoate

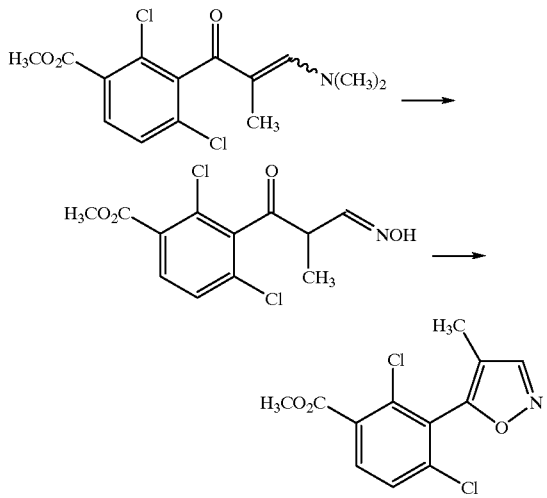

To a mixture of 30 ml dioxane and 16 ml water, was dissolved methyl 2,4-dichloro-3-(2-dimethylaminomethylidene-1-oxopropyl)benzoate in an amount of 7.57 g, and the resulting solution was then added with hydroxylamine hydrochloride in an amount of 1.70 g and further stirred for 17 hours at an ambient temperature. After distillating out the solvent in the solution under reduced pressure, the residue obtained was dissolved in ethyl acetate, and the solution was then washed with saturated saline solution and dried with anhydrous magnesium sulfate. After distillating out the solvent in the solution under reduced pressure, crude oxime-form of the product obtained was dissolved in 30 ml toluene and then stirred for 14.5 hours under reflux and heating following to the addition of p-toluenesulfonic acid in an amount of 0.5 g. The reacted-mixture was cooled, then washed with water and saturated saline solution in turn and dried with anhydrous magnesium sulfate. The solvent used for the mixture was then condensed under reduced pressure, and the residue obtained was purified by using a silica gel column chromatography to obtain an objective product, methyl 2,4-dichloro-3-(4-methylisoxazol-5-yl)benzoate in an amount of 0.83 g.

$^1$H-NMR (CDCl$_3$, δ ppm): 1.97 (3H, s), 3.96 (3H, s), 7.50 (1H, d), 7.89 (1H, d), 8.27 (1H, s).

Reference Example 9

Manufacturing of 2,4-dichloro-3-(4-methylisoxazol-5-yl)benzoic acid

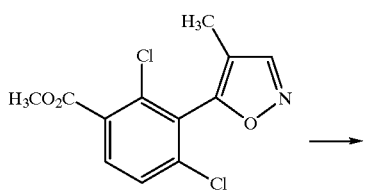

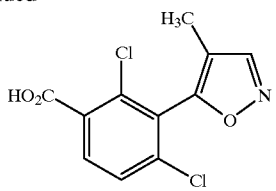

To 20 ml dioxane, was dissolved methyl 2,4-dichloro-3-(4-methylisoxazol-5-yl)benzoate in an amount of 0.83 g, and the resulting solution was then added with concentrated sulfuric acid in an amount of 5 ml and subsequently stirred for 15.5 hours under reflux and heating. After cooling the mixture, dioxane therein was distillated out, and the mixture was then extracted with ethyl acetate. The organic layer obtained was washed with saturated saline solution, then dried with anhydrous magnesium sulfate. The solvent in the layer was condensed under reduced pressure, and the residue obtained was purified by using a silica gel column chromatography to obtain an objective product, 2,4-dichloro-3-(4-methylisoxazol-5-yl)benzoic acid in an amount of 0.48 g in crystalline form. The melting point of the product was found to be in a range of 248–252° C.

Reference Example 10

Manufacturing of methyl 4-methanesulfonyl-2-methyl-3-(3-methyl-1,2-isoxazol-5-yl)benzoate

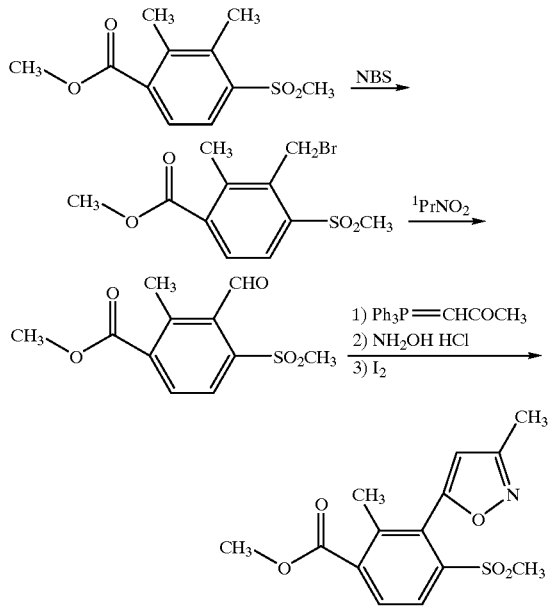

To 80 ml carbon tetrachloride, was dissolved 2,3-dimethyl-4-methanesulfonyl benzoate in an amount of 10.8 g (0.045 mole), and the resulting solution was then added with both N-bromosuccinimide in an amount of 8.3 g (0.047 mole) and benzoyl peroxide in an amount of 0.1 g and was stirred for 3 hours under reflux and heating. After cooling the mixture, insoluble materials therein were separated by filtration, and the filtrate was washed with aqueous solution of sodium hydrogenbisulfite and then dried with anhydrous magnesium sulfate. The solvent in the filtrate was condensed under reduced pressure, and the residue resulted was purified by using a silica gel column chromatography to obtain methyl 3-bromomethyl-4-methanesulfonyl-2-methylbenzoate in an amount of 6.2 g in crystalline form. The yield was 43.4%.

28% methanol solution of sodium methylate in an amount of 2.6 g (0.014 mole) was added into 20 ml methanol, and 2-nitropropane in an amount of 1.3 g (0.015 mole) was fed dropwise into the solution at an ambient temperature. Then, the solution was further added with methyl 3-bromomethyl-4-methanesulfonyl-2-methylbenzoate in an amount of 4.4 g (0.014 mole) and was then stirred for 1 hour under reflux and heating. After cooling the reacted-mixture, the mixture was then added with 50 ml 1N-hydrochloric acid and extracted with ethyl acetate. The ethyl acetate layer obtained was then washed with saturated saline solution and dried with anhydrous magnesium sulfate. The solvent in the mixture was condensed under reduced pressure to obtain methyl 3-formyl-4-methanesulfonyl-2-mthylbenzoate in an amount of 3.1 g in crystalline form. The yield was 88%.

Methyl 3-formyl-4-methanesulfonyl-2-methylbenzoate in an amount of 3.1 g (0.012 mole) was mixed with 30 ml benzene and 2-oxopropylidenetriphenylphosphorane in an amount of 3.85 g (0.012 mole), and the mixture was then stirred for 1 hour under reflux and heating. After cooling the mixture, insoluble materials therein were separated by filtration, and the solvent in the mixture was condensed under reduced pressure to obtain 4-methanesulfonyl-3-(3-oxo-1-butenyl)-2-methylbenzoate. The obtained product was then dissolved in a mixed-solvent of 10 ml ethanol and 10 ml pyridine and was stirred for 1 hour under reflux and heating following to the addition of hydroxylamine hydrochloride in an amount of 1.1 g (0.016 mole). The reacted-mixture was poured into ice water and extracted with ethyl acetate. The ethyl acetate layer obtained was washed with 1N-hydrochloric acid and saturated saline solution respectively and dried with anhydrous magnesium sulfate, and the solvent remained in the mixture was distillated out under reduced pressure. The obtained methyl 4-methanesulfonyl-3-(3-hydroxyimino-1-butenyl)-2-methylbenzoate was dissolved in 15 ml THF, and to the resulting solution, was added 15 ml aqueous solution of sodium hydrogenbicarbonate in an amount of 1.4 g (0.017 mole) and subsequently 12 ml aqueous solution of potassium iodide in an amount of 2.5 g (0.015 mole) and iodine in an amount of 1.1 g (0.05 mole), and the resulting mixture was then allowed to a reflux for 3 hours under heating while blocking light.

The reacted-mixture was poured into ice water and extracted with ethyl acetate following to the addition of sodium hydrogenbisulfite. The organic layer obtained was washed with saturated saline solution and dried with anhydrous magnesium sulfate, and the solvent remained in the mixture was distillated out under reduced pressure to obtain a residue. The residue was then purified by using a silica gel column chromatography to obtain methyl 4-methanesulfonyl-2-methyl-3-(3-methyl-1,2-isoxazol-5-yl)benzoate in an amount of 0.84 g. The yield was 23%.

$^1$H-NMR (CDCl$_3$, δ ppm); 2.36 (3H, s), 2.45 (3H, s), 2.92 (3H, s), 3.98 (3H, s), 6.41 (1H, s), 8.07 (1H, d), 8.16 (1H, d).

Reference Example 11

Manufacturing of methyl 4-methanesulfonyl-2-methyl-3-(3-methyl-1,2-isoxazol-5-yl)benzoate

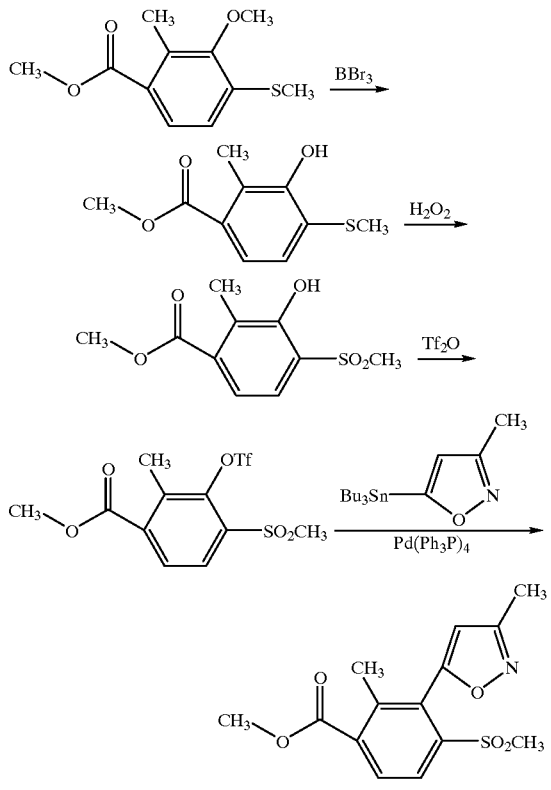

To 90 ml methylene chloride, was dissolved methyl 3-methoxy-2-methyl-4-methylthiobenzoate in an amount of 10 g (0.044 mole), and the resulting solution was then fed dropwise into 90 ml methylene chloride solution of boron tribromide in an amount of 8.4 ml (0.088 mole) at a temperature ranging from 5 to 10° C. After stirring the mixture for 4 hours at an ambient temperature, the mixture was further fed dropwise with 50 ml methanol under cooling with ice and washed with water and then with saturated saline solution. After drying the mixture with anhydrous magnesium sulfate, the solvent remained therein was distillated out under reduced pressure to obtain methyl 3-hydroxy-2-methyl-4-methylthiobenzoate in an amount of 9.2 g. The yield was 98%.

To 50 ml acetic acid, was dissolved methyl 3-hydroxy-2-methyl-4-methylthiobenzoate in an amount of 9.2 g (0.043 mole), and the resulting solution was added with 30% hydrogen peroxide in an amount of 14.8 g (0.130 mole) and then stirred for 3 hours at 80° C. The reacted-mixture was poured into ice water, and the crystals precipitated was filtrated, washed with water and dried to obtain methyl 3-hydroxy-4-methanesulfonyl-2-methylbenzoate in an amount of 8.8 g. The yield was 83%.

To 100 ml methylene chloride, was dissolved methyl 3-hydroxy-4-methanesulfonyl-2-methylbenzoate in an amount of 8.8 g (0.036 mole), and the resulting solution was then added with pyridine in an amount of 8.3 g (0.11 mole), cooled at 0° C. and then added with anhydrous trifluoromethanesulfonic acid in an amount of 12.2 g (0.043 mole). After stirring the mixture for an hour at an ambient temperature, the reacted-mixture was washed with 1N-hydrochloric acid and then with saturated saline solution and dried with anhydrous magnesium sulfate. The solvent remained in the mixture was distillated out under reduced pressure to obtain methyl 4-methanesulfonyl-2-methyl-3-(trifluoromethanesulfonyl)oxybenzoate in an amount of 13.5 g. The yield was 99%.

To 20 ml dioxane, were dissolved 4-methanesulfonyl-2-methyl-3-(trifluoromethanesulfonyl)oxybenzoate in an amount of 1.65 g (4.4 mM) and 3-methyl-5-(tributylstannyl)isoxazol in an amount of 1.97 g (5.3 mM), and the resulting solution was then stirred in an autoclave for 3 hours at 140° C. following to the addition of lithium chloride in an amount of 0.58 g (14 mM), tetrakis-(triphenylphosphine)-paradium-(O) in an amount of 0.1 g and 2,6-di-t-butyl-4-methylphenol in an amount of 0.01 g. After cooling the mixture, insoluble materials therein were separated by filtration, and the residue obtained was purified by using a silica gel column chromatography following to removing of the solvent therein by distillation under reduced pressure to obtain methyl 4-methanesulfonyl-2-methyl-3-(3-methyl-1,2-isoxazol-5-yl)benzoate in an amount of 0.74g. The yield was 55%.

Reference Example 12

Manufacturing of 4-methanesulfonyl-2-methyl-3-(3-methyl-1,2-isoxazol-5-yl)benzoic acid

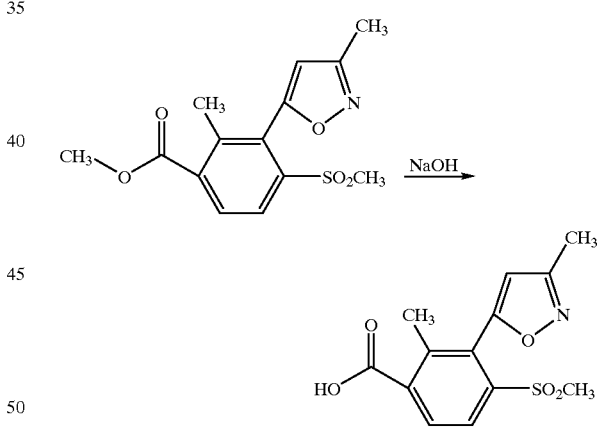

To 30 ml methanol, was dissolved methyl 4-methanesulfonyl-2-methyl-3-(3-methyl-1,2-isoxazol-5-yl)benzoate in an amount of 3.11 g (10.1 mM), and the resulting solution was then stirred over a night at an ambient temperature following to the addition of 30 ml aqueous solution of 1N-sodium hydroxide. The reacted-mixture was poured into ice water and acidified with concentrated hydrochloric acid, and the crystals precipitated were filtrated, washed with water and dried to obtain 4-methanesulfonyl-2-methyl-3-(3-methyl-1,2-isoxazol-5-yl)benzoic acid. The yield was 96%, and the melting point of the product was found to be in a range of 242–244° C.

Reference Example 13

Manufacturing of methyl 2-chloro-4-methoxy-3-methylbenzoate

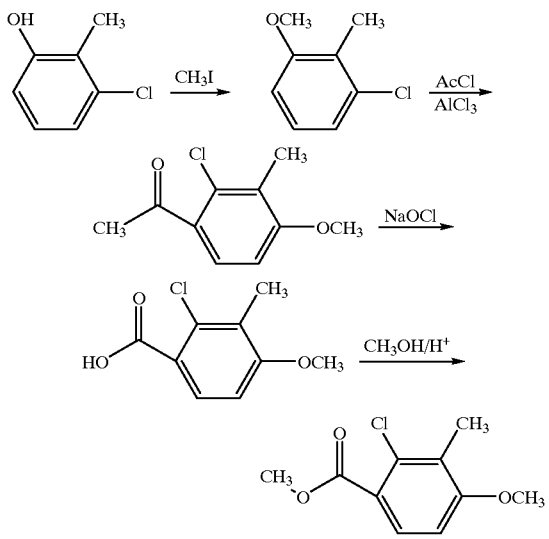

To 100 ml DMF, was dissolved 3-chloro-o-cresol in an amount of 13.6 g (0.095 mole), and the resulting solution was then stirred for 2 hours at 80° C. following to the addition of potassium carbonate in an amount of 14.5 g (0.105 mole) and methyl iodide in an amount of 17.6 g (0.124 mole) into the solution at an ambient temperature. After cooling the mixture, insoluble materials therein were separated by filtration, and the mixture was then poured into water and extracted with ethyl ether. The organic layer obtained was washed with saturated saline solution and dried with anhydrous magnesium sulfate, and the solvent remained in the layer was distillated out to obtain 2-chloro-6-methoxytoluene in an amount of 14.6 g. The yield was 95.4%.

2-Chloro-6-methoxytoluene in an amount of 14.6 g (0.093 mole) was added with 100 ml methylene chloride and aluminium chloride in an amount of 24.9 g (0.187 mole), and acetyl chloride in an amount of 14.6 g (0.187 mole) was fed dropwise into the resulting mixture at 15° C. After stirring the mixture for an hour at an ambient temperature, the mixture was then poured into 1N-hydrochloric acid, and an organic layer obtained was washed with water and dried with anhydrous magnesium sulfate. The solvent remained in the layer was distillated out to obtain 2-chloro-4-methoxy-3-methylacetophenone in an amount of 18.1 g. The yield was 97.7%.

To 90 ml dioxane, was dissolved 2-chloro-4-methoxy-3-methylacetophenone in an amount of 18.1 g (0.0912 mole), and 9% aqueous solution of sodium hypochlorite in an amount of 246 g (0.319 mole) was fed dropwise into the resulting solution at an ambient temperature. After the dropping, the mixture was further stirred for 3 hours at an ambient temperature, and the reacted-mixture was then added with concentrated hydrochloric acid to make it acidic, and the crystals precipitated were filtrated, washed with water and dried to obtain 2-chloro-4-methoxy-3-methylbenzoic acid in an amount of 16.6 g. The yield was 91.2%.

To 150 ml methanol, was dissolved 2-chloro-4-methoxy-3-methylbenzoic acid in an amount of 16.6 g (0.0832 mole), and the resulting solution was stirred for 18 hours under reflux and heating following to the addition of concentrated sulfuric acid in an amount of 1.0 g into the solution. The residue obtained by distillating out the solvent under reduced pressure was dissolved in benzene, washed with 3% aqueous solution of sodium hydrogencarbonate and subsequently with saturated saline solution and dried with anhydrous magnesium sulfate. After distillating out the solvent in the solution under reduced pressure, the crystals remained were washed with methanol to obtain methyl 2-chloro-4-methoxy-3-methylbenzoate in an amount of 13.5 g. The yield was 76.0%.

$^1$H-NMR (CDCl$_3$, δ ppm) 2.21 (3H, s), 3.89 (3H, s), 3.92 (3H, s), 6.78 (1H, d), 7.72 (1H, d).

Reference Example 14

Manufacturing of 2-chloro-4-methoxy-3-(3-methyl-1,2-isoxazol-5-yl) benzoic acid

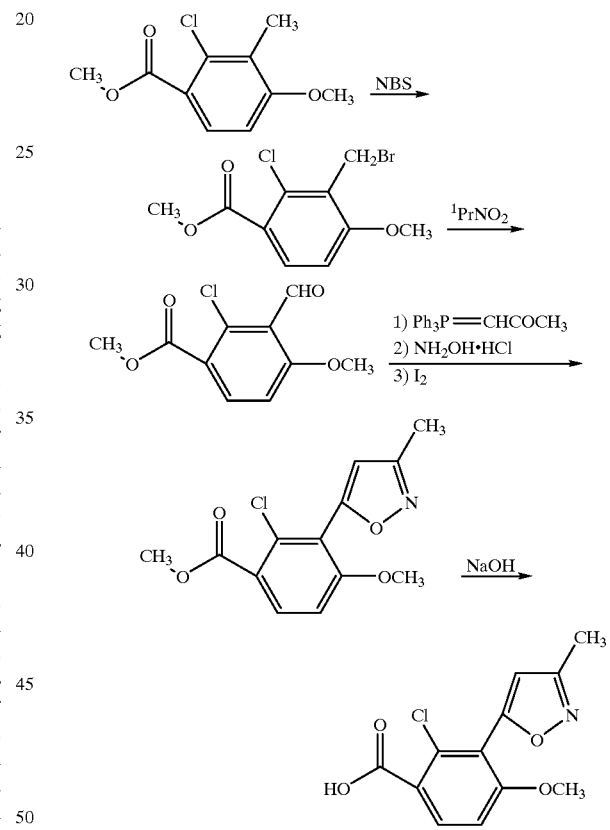

To 50 ml carbon tetrachloride, was dissolved methyl 2-chloro-4-methoxy-3-methylbenzoate in an amount of 5.0 g (0.025 mole), and the resulting solution was then stirred for 4 hours under reflux and heating after the addition of N-bromosuccinimide in an amount of 4.9 g (0.028 mole) and benzoyl peroxide in an amount of 0.1 g into the solution. After cooling the mixture, insoluble material therein were separated by filtration, and the filtrate was washed with aqueous solution of sodium hydrogenbisulfite and then dried with anhydrous magnesium sulfate. The solvent remained in the filtrate was condensed under reduced pressure to obtain methyl 3-bromomethyl-2-chloro-4-methoxybenzoate in an amount of 7.5 g in crude crystalline form.

To 40 ml methanol, was added 28% methanol solution of sodium methylate in an amount of 5.4 g and the resulting mixture was then fed dropwise with 2-nitropropane in an amount of 2.5 g at an ambient temperature. Then, the mixture was further added with methyl 3-bromomethyl-2-chloro-4-methoxybenzoate in an amount of 7.5 g and stirred for an hour under reflux and heating. After cooling the mixture, the reacted-mixture was added with 100 ml 1N-hydrochloric acid and then extracted with ethyl acetate. The ethyl acetate layer obtained was washed with saturated saline solution and dried with anhydrous magnesium sulfate. The solvent remained in the layer was condensed under reduced pressure to obtain crystals. The crystals obtained were then washed with ethyl ether to obtain methyl 2-chloro-3-formyl-4-methoxybenzoate in an amount of 3.1 g in crystalline form. The yield was 54%.

To methyl 2-chloro-3-formyl-4-methoxybenzoate in an amount of 3.08 g (0.0135 mole), were added 30 ml benzene and then 2-oxopropylidenetriphenylphosphorane in an amount of 4.52 g (0.0142 mole), and the resulting mixture was then stirred for an hour under reflux and heating. After cooling the reacted-mixture, insoluble materials therein were separated by filtration, and methyl 2-chloro-3-(3-oxo-1-butenyl)-4-methoxybenzoate obtained by condensing the solvent in the mixture under reduced pressure was dissolved in a mixed-solvent of 25 ml ethanol and 25 ml pyridine, and the resulting solution was stirred for an hour under reflux and heating following to the addition of hydroxylamine hydrochloride in an amount of 3.3 g (0.047 mole) into the solution. The reacted-mixture was poured into ice water and extracted with ethyl acetate, and the ethyl acetate layer obtained was washed with 1N-hydrochloric acid and saturated saline solution, respectively, and dried with anhydrous magnesium sulfate. The solvent remained in the layer was distillated out under reduced pressure to obtain methyl 2-chloro-3-(3-hydroxyimino-1-butenyl)-4-methoxybenzoate. The obtained product was then dissolved in 50 ml THF, whereto 40 ml aqueous solution of sodium hydrogenbicarbonate in an amount of 4.1 g (0.049 mole) was added, and the resulting mixture was then further added with both 35 ml aqueous solution of potassium iodide in an amount of 7.4 g (0.045 mole) and iodine in an amount of 3.4 g (0.014 mole) and then stirred for 3 hours under reflux and heating while blocking light. The reacted-mixture was poured into ice water and extracted with ethyl acetate following to the addition of sodium hydrogensulfite into the mixture. The organic layer obtained was washed with saturated saline solution and dried with anhydrous magnesium sulfate, then solvent remained in the layer was distillated out under reduced pressure. The residue obtained was purified by using a silica gel column chromatography to obtain methyl 2-chloro-4-methoxy-3-(3-methyl-1,2-isoxazol-5-yl) benzoate in an amount of 2.2 g. The yield was 53.5%.

The obtained methyl 2-chloro-4-methoxy-3-(3-methyl-1,2-isoxazol-5-yl)benzoate in an amount of 2.02 g (7.23 mM) was dissolved in 20 ml methanol and then stirred over a night at an ambient temperature following to the addition of 30 ml aqueous solution of 1N-sodium hydroxide into the solution. The reacted-mixture was poured into ice water and acidified with concentrated hydrochloric acid to precipitate the crystals. The crystals obtained were collected by filtration, washed with water and then dried to obtain 2-chloro-4-methoxy-3-(3-methyl-1,2-isoxazol-5-yl)benzoic acid in an amount of 1.87 g. The yield was 97.4%, and the melting point of the product was found to be in a range of 217–220° C.

The compounds according to the present invention have excellent herbicidal activity against weeds grown in upland crop fields either method of soil application or foliar application, in which compounds which demonstrate higher herbicidal effect on various weeds growing in upland crops, such as crabgrass, sedge, velvetleaf and pigweed, and have selectivity in the herbicidal activity which does not give damages to crops, such as maize, cereals, soybean, cotton, etc., are also contained.

In the compounds of the present invention, compounds which have growth regulating activities like growth retarding activity against useful plants, such as agricultural crops, ornamental plants and fruit trees, are contained as well.

Further, in the compounds of the present invention, compounds which have an excellent herbicidal activity against weeds grown in paddy rice fields, such as barnyardgrass, *Cyperus difformis, Sagittaria trifolia*, and *Scirpus juncoides*, and have a characteristic being selectively-safe to rice plants, are also contained.

In addition, the compounds of the present invention can be applied for weed control in orchards, lawns, railways, vacant lands, etc.

Moreover, in the compounds of the present invention, compounds which have plant growth regulating activity, fungicidal activity, insecticidal activity and acaricidal activity, are also contained.

The herbicides according to the present invention comprise one or more compounds of the present invention as the active ingredient(s). At practical application of the compounds of the present invention, the compounds can be applied alone without combining with other elements. Alternatively, the compounds of the present invention can be prepared into any of formulation types normally employed for plant protection chemicals, such as wettable powder, dust, emulsifiable concentrate, suspension and flowable formulation. As an additive or a filler to be used for such formulations, vegetable-origin powder, such as soybean powder and wheat flour, mineral fine powder, such as diatomaceous earth, apatite, gypsum, talc, bentonite, pyrophyllite and clay, and organic or inorganic materials, such as sodium benzoate, urea and Glauber's salt, can be used for a solid-type formulation. In case liquid-type formulations are required, a petroleum fraction, such as kerosine, xylene and solvent naphtha, cyclohexane, cyclohexanone, N,N-dimethylformamide, dimethylsulfoxide, alcohol, acetone, trichloroethylene, methylisobutyl ketone, mineral oil, vegetable oil, water, etc. can be used as a solvent. In order to assure uniform and stable physicochemical properties of such formulations, a surface active agent may be used, if appropriate.

The content of an active ingredient in the herbicide according to the present invention can differ depending upon each of the formulation types as described above. For example, the content can be in a range of from 5 to 90%, and more preferably from 10 to 85%, for a wettable powder formulation; from 3 to 70%, and more preferably from 5 to 60%, for an emulsifiable concentrate formulation; and from 0.01 to 50%, and more preferably from 0.05 to 40%, for a granular formulation.

The wettable powder and the emulsifiable concentrate obtained as described above can be applied in a form of suspension or emulsion after diluting them with appropriate volume of water. The granules obtained as described above can be directly applied to and/or incorporated into soil without dilution prior to or after germination of weed seeds. For practical application of the herbicides according to the present invention, an active ingredient in an appropriate amount more than 0.1 g/ha should be applied.

The herbicide according to the present invention can be used by mixed with any of other known fungicides, insecticides, acaricides, herbicides, plant growth regulators, fertilizers, etc. In particular, it is possible to reduce the dose of the inventive herbicide when it is applied by mixing with other herbicide(s). In this case, such mixing may provide an effect not only to reduce labors required for weeding but also to give higher herbicidal performance due to a synergistic action derived from such herbicides being mixed together. Mixing of the inventive herbicide with a plurality of other known herbicides is also possible.

For examples of the herbicides to be preferably associated with the inventive herbicide, anilide-type herbicides, such as diflufenican and propanil, chloroacetoanilide-type herbicides, such as alachlor and pretilachlor, aryloxy alkane-type herbicides, such as 2,4-D and 2,4-DB, aryloxyphenoxy alkane-type herbicides, such as diclofop-methyl and phonoxaprop-ethyl, arylcarboxylate-type herbicides, such as dicamba and pirithiobac, imidazoline-type herbicides, such as imazaquin and imazethapyr, urea-type herbicides, such as diuron and isoproturon, carbamate-type herbicides, such as chlorpropham and phenmedipham, thiocarbamate-type herbicides, such as thiobencarb and EPTC, dinitroaniline-type herbicides, such as trifluralin and pendimethalin, diphenyl ether-type herbicides, such as acifluorfen and fomesafen; sulfonylurea-type herbicides, such as bensulfuron-methyl and nicosulfuron; triazinone-type herbicides, such as metribuzin and metamitron; triazine-type herbicides, such as atrazine and cyanazine; phosphate-type herbicides, such as glyphosate and glufosinate; quaternary ammonium salt-type herbicides, such as paraguat and difenzoguat; cyclic imide-type herbicides, such as flumiclorac-pentyl and fluthiacet-methyl; and others including isoxaben, ethofumesate, oxacyanone, quinclorac, cromazone, sulcotrione, cynmethyrin, dithiopyr, pyrazolate, flupoxam, bentazone, benfuresate and cyclohexanedione-type herbicides, such as sethoxydim and tralkoxydim, can be given. In addition, a vegetable oil and an oil concentrate may be added to a mixture of the inventive herbicide and one or more of the herbicides exemplified above.

EXAMPLES

Herbicidal Formulations

Now, examples of formulations suitable for the herbicide according to the present invention are given hereinbelow. However, the active ingredients and type and additional part of additives used shall be modified in wide range and shall not be limited to the ones specified in the examples described below. Parts described in the following Formulation Examples means parts by weight.

Formulation Example 7
Wettable Powder

| The inventive compound | 20 parts |
| White carbon | 20 parts |
| Diatomaceous earth | 52 parts |
| Sodium alkylsulfate | 8 parts |

All materials are uniformly mixed and ground to fine powder to obtain a wettable powder formulation comprising an active ingredient at a content of 20%.

Formulation Example 8
Emulsifiable Concentrate

| The inventive compound | 20 parts |
| Xylene | 55 parts |
| N,N-Dimethylformamide | 15 parts |
| Polyoxyethylenephenyl ether | 10 parts |

All materials are mixed and dissolved to obtain an emulsifiable concentrate formulation comprising an active ingredient at a content of 20%.

Formulation Example 9
Granules

| The inventive compound | 5 parts |
| Talc | 40 parts |
| Clay | 38 parts |
| Bentonite | 10 parts |
| Sodium alkylsulfate | 7 parts |

All materials are uniformly mixed, ground to fine powder and granulated into granules having a diameter of from 0.5 to 1.0 mm to obtain a granular formulation comprising an active ingredient at a content of 5%.

ADVANTAGEOUS EFFECT OF THE INVENTION

Now, test examples carried out to show a herbicidal activity of the herbicides according to the present invention are described hereinbelow.

Herbicidal activity is evaluated pursuant to the following criterion, and it is expressed as an index for killed-weeds.
Criterion for Assessment

| % of weeds killed | Index for killed-weeds |
| --- | --- |
| 0% | 0 |
| 20–29% | 2 |
| 40–49% | 4 |
| 60–69% | 6 |
| 80–89% | 8 |
| 100% | 10 |

Indexes 1, 3, 5, 7 and 9 represent an intermediate activity between 0 and 2, 2 and 4, 4 and 6, 6 and 8, and 8 and 10, respectively.

% of Weeds Killed=[(Weight of fresh weeds growing over the ground in non-treated plot−Weight of fresh weeds growing over the ground in a treated-plot)÷(Weight of fresh weeds growing over the ground in non-treated plot)]×100.

Test Example 1
Foliar Application

On surface layer of soil filled into a 200 cm$^2$ planting pot, seeds of velvetleaf, *Xanthium strumarium*, giant fox-tail, oat and maize are respectively planted and are then covered with slight amount of soil to grow them in a greenhouse. When each of the plants has grown to 5 to 25 cm height, respectively, an emulsion of the emulsifiable concentration formulation prepared in the Formulation Example 8 was sprayed to the leaves of the respective plants, at a volume rate of 1,000 liters/ha and at a dose of 63 g/ha as an active ingredient by using a small sprayer. 3 weeks later, effect on the plants and the herbicidal activity were checked, respectively, pursuant to the criterion as described above, showing the results in Table 7.

TABLE 7

| Compound No. | Velvet leaf | Xanthium strumar. | Giant fox-tail | Oat | Maize |
|---|---|---|---|---|---|
| I-4 | 9 | 10 | 7 | 10 | 1 |
| III-4 | 10 | 10 | 10 | 10 | 0 |
| IV-7 | 9 | 9 | 10 | 9 | 0 |
| Reference Compound | 7 | 9 | 3 | 0 | 0 |

Reference Compound: Compound disclosed in WO96/26200 Gazette

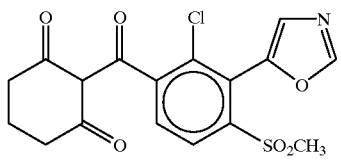

Industrial Use of the Invention

As described above, the compounds specified in the present invention have an excellent herbicidal activity and a property of selectively-safe to the objective crops, and it is promising to provide such compositions comprising the compounds according to the present invention as a herbicide.

What is claimed is:

1. Compound methyl 3-formyl-4-methanesuylfonyl-2-methylbenzoate.

* * * * *

UNITED STATES PATENT AND TRADEMARK OFFICE
CERTIFICATE OF CORRECTION

PATENT NO.   : 6,100,421
DATED        : August 8, 2000
INVENTOR(S)  : Hiroyuki Adachi, et al.

It is certified that error appears in the above-identified patent and that said Letters Patent is hereby corrected as shown below:

Column 4,
Line 51, replace "propalgyloxyiminoethy" with -- propalgyloxyiminoethyl; --.

Column 21,
Line 35, replace "cyclobexane" with -- cyclohexane --.

Column 22,
Line 63, replace "form" with -- form. --.

Column 23,
Line 65, replace "form" with -- form. --.

Column 25,
Line 60, replace "mixture." with -- mixture, --.

UNITED STATES PATENT AND TRADEMARK OFFICE
CERTIFICATE OF CORRECTION

PATENT NO.   : 6,100,421
DATED        : August 8, 2000
INVENTOR(S)  : Hiroyuki Adachi, et al.

Page 2 of 2

It is certified that error appears in the above-identified patent and that said Letters Patent is hereby corrected as shown below:

Column 29,
Table 5, replace

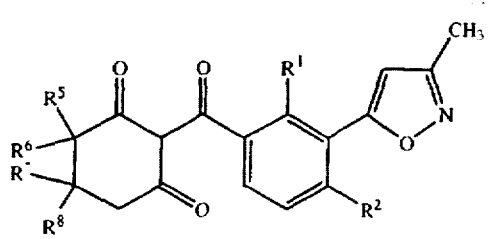

with --

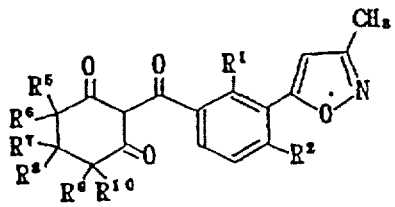

Signed and Sealed this

Twenty-third Day of October, 2001

Attest:

NICHOLAS P. GODICI
Attesting Officer      Acting Director of the United States Patent and Trademark Office